US005997865A

United States Patent [19]
Bennett et al.

[11] Patent Number: 5,997,865
[45] Date of Patent: Dec. 7, 1999

[54] AGONIST ANTIBODIES AGAINST THE FLK2/FLT3 RECEPTOR AND USES THEREOF

[76] Inventors: Brian D. Bennett; Susan D. Broz; William Matthews; Francis C. Zeigler, all of 460 Point San Bruno Boulevard, South San Francisco, Calif. 94080

[21] Appl. No.: 08/434,878

[22] Filed: May 4, 1995

Related U.S. Application Data

[62] Division of application No. 08/222,299, Apr. 4, 1994, Pat. No. 5,635,388.
[51] Int. Cl.$^6$ .......................... A61K 39/395; C07K 16/00
[52] U.S. Cl. ..................................... 424/130.1; 424/143.1; 530/388.22; 530/389.1; 530/387.3
[58] Field of Search .............................. 424/130.1, 143.1; 530/388.22, 389.1, 387.3

[56] References Cited

U.S. PATENT DOCUMENTS

| | | | |
|---|---|---|---|
| 5,087,570 | 2/1992 | Weissman et al. | 424/93.7 |
| 5,199,942 | 4/1993 | Gillis | 604/4 |
| 5,548,065 | 8/1996 | Lemischka, I | 530/388.22 |

FOREIGN PATENT DOCUMENTS

| | | |
|---|---|---|
| 9310136 | 5/1993 | WIPO . |
| WO 94/01576 | 1/1994 | WIPO . |
| WO 94/02157 | 2/1994 | WIPO . |
| WO 95/07348 | 3/1995 | WIPO . |

OTHER PUBLICATIONS

Zeigler et al., "Cellular and Molecular Characterization of the Role of the FLK–2/FLT–3 Receptor Tyrosine Kinase in Hematopoietic Stem Cells" *Blood* 84(8):2422–2430 (1994).
Brizzi et al., "Hematopoietic Growth Factor Receptors" *International Journal of Cell Cloning* 9:274–300 (1991).
Fleming et al., "Functional Heterogeneity is Associated With the Cell Cycle Status of Murine Hematopoietic Stem Cells" *Journal of Cell Biology* 122(4):897–902 (1993).
Hannum et al., "Ligand for FLT3/FLK2 Receptor Tyrosine Kinase Regulates Growth of Haematopoietic Stem Cells and is Encoded by Variant RNAs" *Nature* 368:643 (1994).
Harrison et al., "Primitive Hemopoietic Stem Cells: Direct Assay of Most Productive Populations by Competitive Repopulation With Simple Binomial, Correlation and Covariance calculations" *Experimental Hematology* 21:206–219 (1993).
Jordan et al., "Cellular and Developmental Properties of Fetal Hematopoietic Stem Cells" *Cell* 61:953–963 (1990).
Ogawa, "Differentiation and Proliferation of Hematopoietic Stem Cells" *Blood* 81(11):2844–2853 (1993).
Rosnet et al., "Close Physical Linkage of the FLT1 and FLT3 Genes on Chromosome 13 in Man and Chromosome 5 in Mouse" *Oncogene* 8:173–179 (1993).
Waksal, "Chugai Backs ImClone to the Tune of $35 Million in Stem Cell Research" *Biotechnology News* 13(3) (Feb. 4, 1993).
Andrews et al., "Precursors of colony–forming cells in humans can be distinguished from colony–forming cells by expression of the CD33 and CD34 antigens and light scatter properties" *Journal of Experimental Medicine* 169:1721–1731 (1989).
Baumhueter et al., "Binding of L–selectin to the vascular sialomucin CD34" *Science* 262:436–438 (1993).
Berenson et al., "Antigen CD34+ Marrow Cells Engraft Lethally Irradiated Baboons" *J. Clin. Invest.* 81:951–955 (1988).
Better and Horwitz, "Expression of engineered antibodies and antibody fragments in microorganisms" *Methods in Enzymology* 178:476–496 (1989).
Bloom, B., "The Power of Negative Thinking" *J. Clin. Invest.* 91:1265–1266 (Apr. 1993).
Boggs et al., "Hematopoietic stem cells with high proliferative potential. Assay of their concentration in marrow by the frequency and duration of cure W/Wv mice" *J. Clin. Inv.* 70(2):242–253 (1982).
Civin et al., "Antigenic analysis of hematopoiesis—III. A hematopoietic progenitor cell surface antigen defined by a monoclonal antibody raised against KG–1a cells" *J. Immunol.* 133(1):157–165 (1984).
Hardy et al., "Resolution and characterization of pro–B and pre–pro–B cell stages in normal mouse bone marrow" *Journal of Experimental Medicine* 173:1213–1225 (1991).
Harlow et al. *Antibodies: A Laboratory Manual,* Cold Spring Harbor Laboratory, Chapter 5, pp. 72–76 (1988).
Harrison et al., "Number and continuous proliferative pattern of transplanted primitive immunohematopoietic stem cells" *Proc. Natl. Acad. Sci.* 85(3):822–826 (1988).
Kiefer et al., "Fractionation of mouse bone marrow by adherence separates primitive hematopoietic stem cells from in vitro colony–forming cells and spleen colony–forming cells" *Blood* 78(10):2577–2582 (1991).
Larsson et al., "Characterization of murine thymic stroma–l–cell lines immortalized by temperature–sensitive simian virus 40 large T or adenovirus 5 Ela" *Develop. Immunol.* 1(4):279–293 (1991).
McNiece et al., "The role of recombinant stem cell factor in early B cell development. Synergistic interaction with IL–7" *J. Immunol.* 146:3785–3790 (1991).

(List continued on next page.)

*Primary Examiner*—Lila Feisee
*Assistant Examiner*—Minh-Tam Davis
*Attorney, Agent, or Firm*—Wendy M. Lee

[57] ABSTRACT

Agonist antibodies are disclosed which bind to the extracellular domain of the flk2/flt3 receptor and thereby activate the intracellular kinase domain thereof. The labeled antibodies are useful as diagnostics for detecting the presence of the flk2/flt3 receptor in primitive hematopoietic cells for example. The antibodies are able to cause primitive hematopoietic cells to proliferate and/or differentiate and thereby enhance repopulation of mature blood cell lineages in a mammal which has undergone chemo- or radiation therapy or bone marrow transplantation. The antibodies are further useful for treating mammals which have suffered a decrease in blood cells as a consequence of disease or a hemorrhage, for example.

20 Claims, 4 Drawing Sheets

OTHER PUBLICATIONS

Orlic and Bodine, "Pluripotent Hematopoietic Stem Cells of Low and High Density Can Repopulate W/Wv Mice" *Exp. Hematol.* 20:1291–1295 (1992).

Ploemacher et al., "An in vitro limiting–dilution assay of long–term repopulating hematopoietic stem cells in the mouse" *Blood* 74:2755–2763 (1989).

Rosnet et al., "Hematopoietic receptors of class III receptor–type tyrosine kinases" *Critical Rev. in Oncogenesis* 4:595–613 (1993).

Rosnet et al., "Human FLT3/FLK2 gene: cDNA cloning and expression in hematopoietic cells" *Blood* 82:1110–1119 (1993).

Suda et al., "Proliferative kinetics and differentiation of murine blast cell colonies in culture: evidence for variable CO periods and constant doubling rates of early pluripotent hemopoietic progentiors" *J. Cellular Physiology* 117:308–318 (1983).

Sutherland et al., "Characterization and partial purification of human marrow cells capable of initiating long–term hematopoiesis in vitro" *Blood* 74:1563–1569 (1989).

Osband, ME. et al. 1990 Immunol. Today 11:193–195.

Mamikawa, R. et al. 1995. Blood, 86(10 Suppl. 1) 449A.

Fletdier, FA. et al. 1995 Blood 86(10 Suppl. 1) 21A.

Birg et al., "Expression of the FMS/KIT–Like Gene FLT3 in Human Acute Leukemias of the Myeloid and Lymphoid Lineages" *Blood* 80(10):2584–2593 (1992).

Dosil et al., "Mitogenic Signalling and Substrate Specificity of the Flk2/Flt3 Receptor Tyrosine Kinase of Fibroblasts and Interleukin 3 Dependent Hematopoietic Cells" *Molecular & Cellular Biology* 13(10):6572–6585 (1993).

Kuczynski et al., "Stem Cell Kinase–1 (STK–1), Human Homologue of the Murine FLT3/FLK2 Tyrosine Kinase Receptor Gene, is Expressed on a Wide Variety of Non–Hematopoietic Tumor Cell Types" *Blood* 82(10):PA186 (1993).

Lyman et al., "Characterization of the protein encoded by the flt3 (flk2) receptor–like tyrosine kinase gene" *Oncogene* 8:815–822 (1993).

Lyman et al., "Molecular cloning of a ligand for the flt3/flk–2 tyrosine kinase receptor: a proliferative factor for primitive hematopoietic cells" *Cell* 75:1157–1167 (1993).

Maroc et al., "Biochemical characterization and analysis of the transforming potential of the FLT3/FLK2 Receptor Tyrosine Kinase" *Oncogene* 8:909–918 (1993).

Matthews et al., "A receptor tyrosine kinase specific to hematopoietic stem and progenitor cell–enriched populations" *Cell* 65:1143–1152 (1991).

Orlic et al., "Purification and Characterization of Heterogeneous Pluripotent Hematopoietic Stem Cell Populations Expressing High Levels of c–kit Receptor" *Blood* 82(3):762–770 (1993).

Rosnet et al., "Isolation and Chromosomal Localization of a Novel FMS–like Tyrosine Kinase Gene" *Genomics* 9:380–385 (1991).

Rosnet et al., "Murine Flt3, a gene encoding a novel tyrosine kinase receptor of the PDGFR/CSF1R family" *Oncogene* 6:1641–1650 (1991).

Small et al., "STK–1, the human homolog of Flk–2/Flt–3, is selectively expressed in CD34+ human bone marrow cells and is involved in the proliferation of early progenitor/stem cells" *Proc. Natl. Acad. Sci. USA* 91:459 463 (1994).

Visser et al., "The Expression of Cytokine Receptors by Purified Hematopoietic Stem Cells" *Stem Cells* 11(2):49–55 (1993).

Yarden, "Agonistic Antibodies Stimulate the Kinase Encoded by the neu Protooncogene in Living Cells but the Oncogenic Mutant is Constitutively Active" *Proc. Natl. Acad. Sci. USA* 87:2569–2573 (1990).

AGONIST ANTIBODIES AGAINST THE FLK2/FLT3 RECEPTOR AND USES THEREOF

This is a divisional of application Ser. No. 08/222,299 filed on Apr. 4, 1994 now patented, U.S. Pat No. 5,635,388 which application is incorporated herein by reference and to which application prioity is claimed under 35 USC §120.

FIELD OF THE INVENTION

This application relates to agonist antibodies against the flk2/flt3 receptor and uses thereof. In particular, the invention relates to the use of the antibodies for enhancing the proliferation and/or differentiation of primitive hematopoietic cells.

BACKGROUND OF THE INVENTION

A. Hematopoiesis

The process of blood cell formation whereby red and white blood cells are replaced through the division of cells located in the bone marrow is called hematopoiesis. For a review of hematopoiesis see Dexter and Spooncer (*Ann. Rev. Cell Biol.*, 3:423–441 [1987]).

There are many different types of blood cells which belong to distinct cell lineages. Along each lineage, there are cells at different stages of maturation. Mature blood cells are specialized for different functions. For example, erythrocytes are involved in $O_2$ and $CO_2$ transport; T and B lymphocytes are involved in cell and antibody mediated immune responses, respectively; platelets are required for blood clotting; and the granulocytes and macrophages act as general scavengers and accessory cells. Granulocytes can be further divided into basophils, eosinophils, neutrophils and mast cells.

Each of the various blood cell types arises from pluripotent or totipotent stem cells which are able to undergo self-renewal or give rise to progenitor cells or Colony Forming Units (CFU) that yield a more limited array of cell types. As stem cells progressively lose their ability to self-renew, they become increasingly lineage restricted. It has been shown that stem cells can develop into multipotent cells (called "CFC-Mix" by Dexter and Spooncer, supra). Some of the CFC-Mix cells can undergo renewal whereas others lead to lineage-restricted progenitors which eventually develop into mature myeloid cells (e.g., neutrophils, megakaryocytes, macrophages, basophils and erythroid cells). Similarly, pluripotent stem cells are able to give rise to PreB and PreT lymphoid cell lineages which differentiate into mature B and T lymphocytes, respectively. Progenitors are defined by their progeny, e.g., granulocyte/macrophage colony-forming progenitor cells (GM-CFU) differentiate into neutrophils or macrophages; primitive erythroid burst-forming units (BFU-E) differentiate into erythroid colony-forming units (CFU-E) which give rise to mature erythrocytes. Similarly, the Meg-CFU, Eos-CFU and Bas-CFU progenitors are able to differentiate into megakaryocytes, eosinophils and basophils, respectively.

The number of pluripotent stem cells in the bone marrow is extremely low and has been estimated to be in the order of about one per 10,000 to one per 100,000 cells (Boggs et al., *J. Clin. Inv.*, 70:242 [1982] and Harrison et al., *PNAS*, 85; 822 [1988]). Accordingly, characterization of stem cells has been difficult. Therefore, various protocols for enriching pluripotent stem cells have been developed. See, for example, Matthews et al., *Cell*, 65:1143–1152 [1991]; WO 94/02157; Orlic et al., *Blood*, 82(3):762–770 [1993]; and Visser et al., *Stem Cells*, 11(2):49–55 [1993].

Various lineage-specific factors have been demonstrated to control cell growth, differentiation and the functioning of hematopoietic cells. These factors or cytokines include the interleukins (e.g., IL-3), granulocyte-macrophage colony-stimulating factor (GM-CSF), macrophage colony-stimulating factor (M-CSF), granulocyte colony-stimulating factor (M-CSF), erythropoietin (Epo), lymphotoxin, steel factor (SLF), tumor necrosis factor (TNF) and gamma-interferon. These growth factors have a broad spectrum of activity, from generalized to lineage-specific roles in hematopoiesis, or a combination of both. For example, IL-3 appears to act on multipotent stem cells as well as progenitors restricted to the granulocyte/macrophage, eosinophil, megakaryocyte, erythroid or mast cell lineages. On the other hand, Epo generally acts on fairly mature erythroid progenitor cells.

B. Tyrosine Kinases

Many cytokines involved in hematopoietic development stimulate receptor protein tyrosine kinases (pTKs). For example, the c-kit pTK and its cognate ligand (KL) have been shown to play a role in hematopoiesis. Tyrosine kinases catalyze protein phosphorylation using tyrosine as a substrate for phosphorylation. Members of the tyrosine kinase family can be recognized by the presence of several conserved amino acid regions in the tyrosine kinase catalytic domain (Hanks et al., *Science*, 241:42–52 [1988]). Receptor protein tyrosine kinases share a similar architecture, with an intracellular catalytic portion, a hydrophobic transmembrane domain and an extracellular ligand-binding domain. The extracellular domains (ECDs), which are responsible for ligand binding and transmission of biological signals, have been shown to be composed of a number of distinct structural motifs. The intracellular domain comprises a catalytic protein tyrosine kinase. The binding of ligand to the extracellular portion is believed to promote dimerization of the pTK resulting in transphosphorylation and activation of the intracellular tyrosine kinase domain (see Schlessinger et al., *Neuron*, 9:383–391 [1992]).

C. Flk2/Flt3 Receptor

A murine gene encoding a pTK which is expressed in cell populations enriched for stem cells and primitive uncommitted progenitors has been identified and is called "fetal liver kinase-2" or "flk-2" by Matthews et al. in *Cell*, 65:1143–52 [1991]. Rosnet et al. independently identified partial cDNA sequences for the same gene, which they call "flt3", from murine and human tissues (*Genomics*, 9:380–385 [1991]). The full length flt3 sequence has been published by Rosnet et al. in *Oncogene*, 6:1641–1650 [1991]. The sequence for human flk2 is disclosed in WO 93/10136. Kuczynski et al. refer to a gene called "STK-1" which is said to be the human homologue of murine flk2/flt3 (*Blood*, 82(10):PA486 [1993]).

Matthews et al. isolated the flk2 cDNA from stem cell-enriched hematopoietic tissue. In order to enrich for stem cells, murine fetal liver cells were fractionated using the AA4.1 monoclonal antibody and a cocktail of antibodies raised against specific differentiation antigens, collectively called "Lin". Flk-2 was found to be expressed in $AA4^+$, $AA4^+$ $Lin^{lo}$ and $AA4^+$ $Lin^{br}$ cells, but not in $AA4^-$ cells. The $AA4^+$ $Lin^{lo}$ population contained all of the long-term pluripotent stem cells. The $AA4^+$ $Lin^{br}$ population was depleted of pluripotent stem cells but contained multipotent progenitors. The $AA4^-$ population was devoid of primitive clonogenic cells but contained less primitive progenitors such as the CFU-E. Expression of flk2 in $AA4^+$ $Sca^+$ and $AA4^+$ $Sca^+$ $Lin^{lo}$ populations, which are considered to be highly enriched stem cell populations, was further demonstrated.

Additional expression of flk2 in the day 14 thymus (at which stage the thymocyte population is highly enriched in primitive precursors) was studied. Flk2 mRNA was expressed in the most immature T lymphocyte population (CD4$^-$8$^-$ Thy-1$^{lo}$/IL-2R$^-$). Overall, the results of the experiments described in Matthews et al. indicate that flk2 is expressed in the most primitive stem/progenitor hematopoietic cells.

Poly(A)$^+$ RNA expression in fetal and adult tissues was also investigated by Matthews et al. Expression of flk2 mRNA in the fetal brain and liver as well as adult brain and bone marrow tissues was observed. Rosnet et al. similarly observed that the flt3 gene is expressed in placenta and in various adult tissues including gonads and the brain as well as hematopoietic cells (*Oncogene,* 6:1641–1650 [1991]). The flt3 transcript identified by Rosnet et al. was 3.7 kb long, except in the testis, where two shorter transcripts were identified.

Small et al. (*USA PNAS,* 91:459–463 [1994]) have shown that antisense oligonucleotides directed against the human homologue of the flk2/flt3 gene inhibit colony formation in long term bone marrow cultures, which results further indicate that flk2/flt3 may transduce growth signals in hematopoietic stem cells.

WO 94/01576 refers to a soluble form of the flk2/flt3 receptor, designated flk-2ws, encoded by a 1.9 kb DNA fragment.

Dosil et al. prepared a chimeric receptor which consisted of the extracellular ligand-binding domain of the human fms pTK and the transmembrane and tyrosine kinase domains of murine flk2/flt3. It was shown that the chimeric receptor conferred transformed properties to NIH 3T3 cells and sustained long-term proliferation of the Ba/F3 cell line (a murine IL-3-dependent hematopoietic cell line which generates B lymphocytes in vivo) in the absence of IL-3 (*Mol. Cell. Biol.,* 13(10):6572–6585 [1993]). It was shown that flk2/flt3 interacts with the p85 subunit of PI 3'-kinase and induced tyrosine phosphorylation of PLCγ, GAP and Shc proteins. PI 3'-kinase, PLCγ, GAP and Shc proteins are intracellular substrate proteins which are known to associate with pTKs.

The flk2/flt3 receptor is structurally related to subclass III pTKs such as α and β platelet-derived growth factor receptors (PDGF-R), colony-stimulating factor (CSF-1, also known as macrophage colony stimulating factor, M-CSF) receptor (c-fms) and Steel factor (also known as mast cell growth factor, stem cell factor or kit ligand) receptor (c-kit). These receptors form a subfamily of pTKs which have five immunoglobulin-like segments in their ECDs and the intracellular catalytic domains thereof are interrupted by a specific hydrophilic "interkinase" sequence of variable length. The genes of this pTK subclass appear to have major growth and/or differentiation functions in various cells, particularly in the hematopoietic system and in placental development (see Rosnet et al. in *Genomics,* supra). Signaling through the c-fms receptor regulates the survival, growth and differentiation of monocytes. Steel factor (SLF) which interacts with c-kit stimulates the proliferation of cells in both myeloid and lymphoid lineages and is a potent synergistic factor in combination with other cytokines (Lyman et al., *Oncogene,* 8:815–822 [1993]).

The flk2/flt3 pTK is mentioned by various other authors. See, for example, Orlic et al., supra; Birg et al., *Blood,* 80(10):2584–2593 [1992]; and Visser et al., supra.

Lyman et al. refer to the molecular cloning of the transmembrane ligand for flk2/flt3 which is shown to activate the flk2/flt3 receptor (*Cell,* 75:1157–1167 [1993]). The protein was found to be similar in size and structure to the cytokines, M-CSF and SLF. The flk2/flt3 ligand was shown to increase thymidine incorporation in early hematopoietic cell precursors.

In their earlier publication, Lyman et al. refer to the production of rabbit polyclonal antibodies against the interkinase domain or C-terminus of flk2/flt3 which immunoprecipitated a major band of 143 kDa and a more diffuse band of 158 kDa. A C-terminal peptide of the flt3 sequence containing the final 22 amino acids thereof was used to generate the antisera. See Lyman et al., *Oncogene,* 8:815–822 [1993]. Maroc et al. also refer to the production of polyclonal antibodies against the C-terminal kinase domain of flk2/flt3 for use in studying the biochemical features of this protein (see *Oncogene,* 8:909–918 [1993]). Polyclonal rabbit immune serum was directed against a fusion of the interkinase domain of flk2/flt3 with TrpE. However, agonist antibodies which are able to activate the flk2/flt3 receptor have heretofore not been disclosed.

D. Therapeutic Implications

Chemo- and radiation therapies cause dramatic reductions in blood cell populations in cancer patients. At least 500,000 cancer patients undergo chemotherapy and radiation therapy in the US and Europe each year and another 200,000 in Japan. Bone marrow transplantation therapy of value in aplastic anemia, primary immunodeficiency and acute leukemia (following total body irradiation) is becoming more widely practiced by the medical community. At least 15,000 Americans have bone marrow transplants each year. Other diseases can cause a reduction in entire or selected blood cell lineages. Examples of these conditions include anemia (including macrocytic and aplastic anemia); thrombocytopenia; hypoplasia; immune (autoimmune) thrombocytopenic purpura (ITP); and HIV induced ITP.

A pharmaceutical product which is able to enhance reconstitution of blood cell populations in these patients would clearly be of therapeutic benefit.

Accordingly, it is an object of the present invention to provide agonist antibodies against the flk2/flt3 receptor. The labeled antibodies can be used to detect the flk2/flt3 receptor in biological samples.

It is a further object of this invention to provide a method for enhancing the proliferation or differentiation of primitive hematopoietic cells, thus enhancing repopulation of mature blood cell lineages. This is desirable where a mammal has suffered a decrease in hematopoietic or mature blood cells as a consequence of disease, radiation or chemotherapy. This method is also useful for generating mature blood cell lineages from hematopoietic cells ex vivo.

These and other objects will be apparent to the ordinary artisan upon consideration of the specification as a whole.

SUMMARY OF THE INVENTION

These objects are accomplished, in one aspect, by providing agonist antibodies against flk2/flt3.

In another aspect, the present invention is based on the observation that such agonist antibodies against flk2/flk3 are able to enhance proliferation and differentiation of primitive hematopoietic cells.

Accordingly, the present invention concerns a method for enhancing proliferation or differentiation of primitive hematopoietic cells comprising contacting the primitive hematopoietic cells with an effective amount of an agonist antibody against the flk2/flt3 receptor.

In a preferred embodiment, the agonist antibody is a monoclonal antibody directed against an epitope in the extracellular domain of flk2/flt3.

In a still further aspect, the present invention concerns a method of enhancing repopulation of blood cell lineages in a mammal comprising administering to the mammal a therapeutically effective amount of an agonist antibody against the flk2/flt3 receptor.

BRIEF DESCRIPTION OF THE DRAWINGS

FIGS. 2A–D show fractionation of AA4$^+$ cells from day 14 gestation fetal liver. AA4$^+$ cells were enriched by immune-panning and were subsequently stained using Sca-1, CD34, flk-2 and c-kit antibodies. AA4$^+$ cells were stained for flk-2 and Sca-1 (FIG. 2A); c-kit and CD34 (FIG. 2B); flk-2 and CD34 (FIG. 2C); and flk-2 and c-kit (FIG. 2D). FIGS. 2E & 2F depict fractionation of Lin$^{lo}$ bone marrow progenitor cells with flk-2, CD34 and Sca-1 antibodies. Lin$^{lo}$ bone marrow progenitor cells were isolated by indirect magnetic bead panning. The Lin cocktail was comprised of RA3-GB2, GR-1, MAC-1, CD4, CD8, Ter-119 and CD5. The Lin$^{lo}$ bone marrow cells were stained for flk-2 and CD34 (FIG. 2E); and Sca-1 and flk-2 (FIG. 2F), (shown as a dot plot because of the very small population of Lin$^{lo}$Sca$^+$ flk-2$^+$ cells in the marrow). These experiments were repeated a minimum of four times and the staining profiles were identical.

FIGS. 3C and 3D illustrate corresponding red fluorescence histograms obtained following acridine orange for AA4$^+$ SCA$^+$ flk-2$^-$ (FIG. 3C) and for AA4$^+$ SCA$^+$ flk-2$^+$ enriched populations (FIG. 3D). The cursor illustrated the fluorescence intensity utilized to discriminate G$_0$ (lower fluorescence intensity) from cycling cells. The percentages of cells in each phase of the cell cycle are provided in the inset.

DETAILED DESCRIPTION OF THE PREFERRED EMBODIMENTS

I. Definitions

Figure 1:
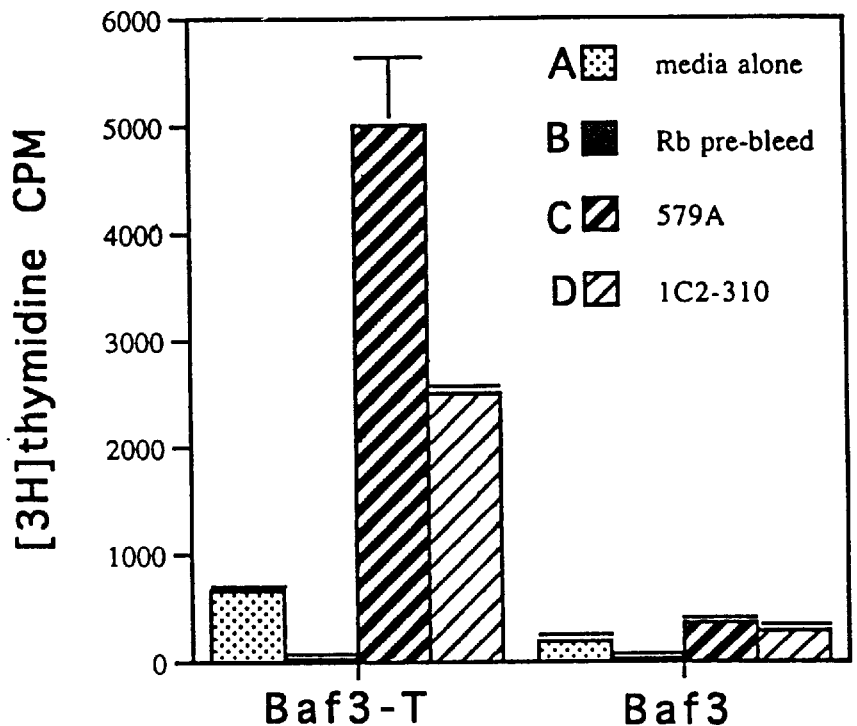
FIG. 1 depicts the results of the thymidine incorporation assay using flk2/flt3 receptor transfected into the IL-3 dependent cell line, 32D. In the assay, cells were starved of IL-3 overnight and then stimulated for 24 hours and thymidine incorporation was determined. Both transfected BAF-3 cells (BAF-3T) and the parent BAF-3 cell line were stimulated with (a) media alone (b) rabbit pre-immune sera (c) 579A polyclonal antibody or (d) IC2-310 agonist monoclonal antibody.

In general, the following words or phrases have the indicated definition when used in the description, examples, and claims:

The term "flk2/flt3" when used herein refers to a polypeptide molecule that comprises the full-length, native amino acid sequence encoded by the gene variously known as flk2, flt3 and STK-1, from any species, including the murine and human polypeptides having the amino acid sequences of SEQ ID NO: 2 and SEQ ID NO: 4, respectively, or amino acid sequence variants of such polypeptides. Generally, the DNA encoding such variants is capable of hybridizing under stringent conditions with the native flk2/flt3 DNA sequence. This definition specifically encompasses soluble forms of flk2/flt3, from natural sources (see, e.g., WO 94/01576), synthetically produced in vitro or obtained by genetic manipulation including methods of recombinant DNA technology, as well as various chain combinations of such polypeptides. The amino acid sequence variants preferably share at least about 65% sequence homology, and more preferably at least about 75% sequence homology with any domain of a native flk2/flt3 amino acid sequence. The definition specifically covers variously glycosylated and unglycosylated forms of flt2/flt3. Flk2/flt3 receptors from non-human or non-murine mammalian (e.g., bovine, equine, porcine, etc.) species can, for example, be obtained by cross-species hybridization, using probes obtained from the murine or human DNA sequence (SEQ ID NOS: 1 and 3, respectively) as hybridization probes to isolate the cDNA from the mammalian cDNA libraries.

Stringent conditions are those that (1) employ low ionic strength and high temperature for washing, for example, 0.015 M NaCl/0.0015 M sodium citrate/0.1% NaDodSO$_4$ at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

The expression "extracellular domain" or "ECD" when used herein in relation to the flk2/flt3 receptor refers to any polypeptide sequence that shares a ligand binding function of the extracellular domain of the flk2/flt3 receptor. Ligand binding function of the extracellular domain refers to the ability of the polypeptide to bind at least one flk2/flt3 ligand (e.g., the ligand disclosed by Lyman et al., in *Cell*, supra). Accordingly, it is not necessary to include the entire extracellular domain since smaller segments are commonly found to be adequate for ligand binding. The truncated extracellular domain is generally soluble. This term encompasses polypeptide sequences in which the hydrophobic transmembrane sequence (and, optionally, 1–20 amino acids C-terminal and/or N-terminal of the transmembrane domain) of the mature pTK has been deleted. Thus, the soluble extracellular domain-containing polypeptide can comprise the extracellular domain and the cytoplasmic domain of the flk2/flt3 receptor. Alternatively, in the preferred embodiment, the polypeptide comprises only the extracellular domain of flk2/flt3. Generally, the ECD will comprise at least amino acid residues 1 to 542 of SEQ ID NOS: 2 or 4.

"Antibodies (Abs)" are proteins which exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V$_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.*, 186:651–663 [1985]; Novotny and Haber, *Proc. Natl. Acad. Sci, USA*, 82:4592–4596 [1985]).

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv), so long as they exhibit the desired biological activity.

The term "variable" refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat, E.A. et al., *Sequences of Proteins of Immunological Interest* National Institute of Health, Bethesda, Md. [1987]). The constant domains are not involved directly in binding an antibody to an antigen, but exhibit various effector functions, such as participation of the antibody in antibody-dependent cellular toxicity.

Papain digestion of antibodies produces two identical antigen binding fragments, called Fab fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$–$V_L$ diner. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The light chains of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature*, 256:495 [1975], or may be made by recombinant DNA methods [see, e.g., U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 (Cabilly et al.; Morrison et al., *Proc. Natl. Acad. Sci. USA*, 81:6851–6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature*, 321:522–525 [1986]; Reichmann et al., *Nature*, 332:323–329 [1988]; and Presta, *Curr. Op. Struct. Biol.*, 2:593–596 [1992]).

By "agonist antibody" is meant an antibody which is able to bind to, and activate flk2/flt3. For example, the agonist may bind to the extracellular domain of flk2/flt3 and thereby cause dimerization of this receptor, resulting in transphosphorylation and activation of the intracellular catalytic kinase domain thereof. Consequently, this may result in stimulation of growth and/or differentiation of cells expressing the receptor. As disclosed herein, these cells will generally comprise primitive stem/progenitor hematopoietic cells and thus the agonist antibodies will cause primitive hematopoietic cells to differentiate and/or proliferate which will generally lead to a repopulation of mature blood cell lineages. The agonist antibodies herein are preferably against epitopes within the extracellular domain of flk2/flt3. The term "agonist antibody" covers anti-flk2/flt3 agonist monoclonal antibodies and anti-flk2/flt3 agonist antibody compositions with polyepitopic specificity. In the preferred embodiment of the invention, the antibodies are monoclonal antibodies.

In the most preferred embodiment, the monoclonal antibodies have the same biological characteristics as the monoclonal antibody produced by the hybridoma cell line deposited under American Type Culture Collection Accession No. ATCC HB 11,557. By "biological characteristics" is meant the in vitro and/or in vivo activities of the monoclonal antibody, e.g., ability to activate the kinase domain of flk2/flt3, ability to stimulate cell growth and/or differentiation of primitive hematopoietic cells and binding characteristics of the antibody, etc. Accordingly, the antibody preferably binds to substantially the same epitope as the anti-flk2/flt3 monoclonal antibody disclosed herein. Most preferably, the antibody will also have substantially the same, or greater, antigen binding affinity of the anti-flk2/flt3 monoclonal antibody disclosed herein. To determine whether a monoclonal antibody has the same specificity as the anti-flk2/flt3 antibody specifically disclosed (i.e., the antibody having the ATCC deposit No. HB 11,557), one can, for example, use a competitive ELISA binding assay.

An "isolated" polypeptide (e.g., antibody) means polypeptide which has been identified and separated and/or recovered from a component of its natural environment. Contaminant components of its natural environment are materials which would interfere with any diagnostic or therapeutic use for the polypeptide, and may include enzymes, hormones, and other proteinaceous or nonproteinaceous solutes. In preferred embodiments, for example, a polypeptide product comprising a monoclonal antibody of the present invention will be purified from a cell culture or other synthetic environment (1) to greater than 95% by weight of protein as determined by the Lowry method, and most preferably more than 99% by weight; (2) to a degree sufficient to obtain at least 15 residues of N-terminal or internal amino acid sequence by use of a gas- or liquid-phase sequenator (such as commercially available Applied Biosystems sequenator Model 470, 477, or 473), or (3) to homogeneity by SDS-PAGE under reducing or nonreducing conditions using Coomassie blue or, preferably, silver stain.

The term "therapeutically effective amount" is used to refer to an amount of any given molecule sufficient for the prevention or treatment of a specified physiological condition or symptom. The therapeutically effective amount of the agonist antibody to be administered will be governed by considerations such as the disorder being treated, the particular mammal being treated, the clinical condition of the individual patient, the cause of the disorder, the site of delivery of the agent, the method of administration, the scheduling of administration, and other factors known to medical practitioners and is the minimum amount necessary to repopulate mature blood cell lineages in patients having undergone chemo- or radiation therapy or bone marrow transplantation therapy or any of the other conditions or diseases mentioned herein.

By "primitive hematopoietic cells" is meant the most primitive or most uncommitted blood cells of the hematopoietic system. The blood cells may comprise totipotent stem cells and/or cells which are slightly committed to a particular blood cell lineage (i.e., multipotent cells).

The term "mammal" refers to any animal classified as a mammal, including humans, domestic and farm animals, and zoo, sports, or pet animals, such as dogs, horses, cats, cows, etc. Preferably, the mammal herein is human.

The term "cytokine" is a generic term for proteins released by one cell population which act on another cell as intercellular mediators. Examples of such cytokines are lymphokines, monokines, and traditional polypeptide hormones. Included among the cytokines are growth hormone, insulin-like growth factors, human growth hormone, N-methionyl human growth hormone, bovine growth hormone, parathyroid hormone, thyroxine, insulin, proinsulin, relaxin, prorelaxin, glycoprotein hormones such as follicle stimulating hormone (FSH), thyroid stimulating hormone (TSH), and luteinizing hormone (LH), hematopoietic growth factor, hepatic growth factor, fibroblast growth factor, prolactin, placental lactogen, tumor necrosis factor-alpha and -beta, mullerian-inhibiting substance, mouse gonadotropin-associated peptide, inhibin, activin, vascular endothelial growth factor, integrin, thrombopoietin, nerve growth factors such as NGF-$\beta$, platelet-growth factor, transforming growth factors (TGFs) such as TGF-$\alpha$ and TGF-$\beta$, insulin-like growth factor-I and -II, erythropoietin (EPO), osteoinductive factors, interferons such as interferon-alpha, -beta, and -gamma, colony stimulating factors (CSFs) such as macrophage-CSF (M-CSF), granulocyte-macrophage-CSF (GM-CSF), and granulocyte-CSF (G-CSF), interleukins (ILs) such as IL-1, IL-1$\alpha$, IL-2, IL-3, IL-4, IL-5, IL-6, IL-7, IL-8, IL-9, IL-11, IL-12 and other polypeptide factors including LIF, SCF, and kit-ligand. As used herein the foregoing terms are meant to include proteins from natural sources or from recombinant cell culture. Similarly, the terms are intended to include biologically active equivalents; e.g., differing in amino acid sequence by one or more amino acids or in type or extent of glycosylation.

II. Production of Antibodies
(a) Polyclonal Antibodies

Polyclonal antibodies to flk2/flt3 are generally raised in animals by multiple subcutaneous (sc) or intraperitoneal (ip) injections of the flk2/flt3 and an adjuvant. It may be useful to conjugate the flk2/flt3 or a fragment containing the target amino acid sequence (e.g., the ECD of flk2/flt3) to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to ¹⁄₁₀ the original amount of conjugate in Freund's complete adjuvant by subcutaneous injection at multiple sites. 7 to 14 days later the animals are bled and the serum is assayed for flk2/flt3 antibody titer. Animals are boosted until the titer plateaus. Preferably, the animal is boosted with a conjugate of the same flk2/flt3 to a different protein and/or to the same protein through a different cross-linking reagent. Conjugates also can be made in recombinant cell culture as protein fusions. Also, aggregating agents such as alum are used to enhance the immune response.

(b) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the flk2/flt3 monoclonal antibodies of the invention may be made using the hybridoma method first described by Kohler & Milstein, *Nature*, 256:495 [1975], or may be made by recombinant DNA methods (U.S. Pat. No. 4,816,567 (Cabilly et al.)).

In the hybridoma method, a mouse or other appropriate host animal, such as hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, *Monoclonal Antibodies; Principles and Practice*, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 [1984]; Brodeur, et al., *Monoclonal Antibody Production Techniques and Applications*, pp.51–63, Marcel Dekker, Inc., New York, 1987).

Culture medium in which hybridoma cells are growing is assayed for production of monoclonal antibodies directed against flk2/flt3. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, *Anal. Biochem.*, 107:220 [1980].

After hybridoma cells are identified that produce antibodies of the desired specificity, affinity, and/or activity, the clones may be subcloned by limiting dilution procedures and grown by standard methods (Goding, supra). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, (Cabilly et al., supra; Morrison, et al., *Proc. Nat. Acad. Sci.*, 81:6851 [1984]), or by covalently joining to the immunoglobulin coding sequence all or part of the coding sequence for a non-immunoglobulin polypeptide.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for the flk2/flt3 receptor and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; radioactive isotopic labels, such as, e.g., $^{125}$I, $^{32}$P, $^{14}$C, or $^{3}$H, or an enzyme, such as alkaline phosphatase, beta-galactosidase or horseradish peroxidase.

Any method known in the art for separately conjugating the antibody to the detectable moiety may be employed, including those methods described by Hunter, et al., *Nature*, 144:945 [1962]; David, et al., *Biochemistry*, 13:1014 [1974]; Pain, et al., *J. Immunol. Meth.*, 40:219 [1981]; and Nygren, *J. Histochem. and Cytochem.*, 30:407 [1982].

The antibodies of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc., 1987).

Competitive binding assays rely on the ability of a labeled standard (which may be a flk2/flt3 receptor or an immunologically reactive portion thereof) to compete with the test sample analyte (flk2/flt3) for binding with a limited amount of antibody. The amount of flk2/flt3 in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

(c) Humanized and Human Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 [1986]; Riechmann et al., *Nature*, 332:323–327 [1988]; Verhoeyen et al., *Science*, 239:1534–1536 [1988]), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the so called "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., *J. Immunol.*, 151:2296 [1993]; Chothia and Lesk, *J. Mol. Biol.*, 196:901 [1987]). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 [1992]; Presta et al., *J. Immnol.*, 151:2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see WO 94/04679 published Mar. 3, 1994, the disclosure of which is incorporated herein by reference.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551–255 [1993]; Jakobovits et al., *Nature*, 362:255–258 [1993]; Bruggermann et al., *Year in Immuno.*, 7:33 [1993]. Human antibodies can also be produced in phage display libraries (Hoogenboom and Winter, *J. Mol. Biol.*, 227:381 [1991]; Marks et al., *J. Mol. Biol.*, 222:581 [1991]).

The techniques of Cote et al. and Boerner et al. are also available for the preparation of human monoclonal antibodies (Cote et al., *Monoclonal Antibodies and Cancer Therapy*, Alan R. Liss, p. 77 [1985] and Boerner et al., *J. Immunol.*, 147(1):86–95 [1991]).

(d) Screening for Agonist Antibodies

In order to screen for antibodies which are agonists for the flk2/flt3 receptor, the tyrosine phosphorylation assay of Holmes et al. (*Science*, 256:1205–1210 [1992]) is available. This assay is described in detail in Example 1C herein. Alternatively, a thymidine incorporation assay using the flk2/flt3 receptor transfected into an IL-3 dependent cell line can be performed. (See Example 1C herein).

III. Therapeutic uses for Anti-flk2/flt3 Agonist Antibodies

The agonist antibodies of the present invention can be used to enhance repopulation of mature blood cell lineages in cells having undergone chemo- or radiation therapy or bone marrow transplantation therapy. Generally, the antibodies will act via an enhancement of the proliferation and/or differentiation of primitive hematopoietic cells. The antibodies may, for example, enhance the proliferation and differentiation of myeloid and lymphoid lineages. The agonist antibodies are similarly useful for treating diseases characterized by a decrease in blood cells. Examples of these diseases include: anemia (including macrocytic and aplastic anemia); thrombocytopenia; hypoplasia; immune (autoimmune) thrombocytopenic purpura (ITP); and HIV induced ITP. Also, the agonist antibodies are useful for treating patients having suffered a hemorrhage.

The antibodies disclosed herein may be administered to a human patient, in a pharmaceutically acceptable dosage form, suitable for intravenous, subcutaneous or intramuscular administration. Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. The molecules will typically be formulated in such vehicles at a concentration of about 0.1 mg/ml to 100 mg/ml.

Pharmaceutical compositions may be prepared and formulated in dosage forms by methods known in the art; for example, see Remington's Pharmaceutical Sciences, Mack Publishing Company, Easton, Pa., 15th Edition 1975.

From about 1 to 500 μg/kg, preferably about 1 to 100 μg/kg, more preferably about 10 to 100 μg/kg, most preferably about 10 to 50 μg/kg of antibody is a suitable initial candidate dosage for administration to the patient, whether, for example, by one or more separate administrations, or by continuous infusion. For repeated administrations over several days or longer, depending on the condition, the treatment is repeated until a desired suppression of disease symptoms occurs or the desired improvement in the patient's condition is achieved. The dose may be readministered at intervals ranging from once a week to once every six months. The determination of the optimum dosage and of optimum route and frequency of administration is well within the knowledge of those skilled in the art. Similarly, dosages for other molecules within the scope of the present invention can be determined without excessive experimentation.

The treatment according to the present invention can be combined with other therapies for enhancing repopulation of hematopoietic blood cell lineages. For example, the antibodies can be co-administered with other cytokines or hematopoietic growth factors which are capable of enhancing the proliferation and/or differentiation of hematopoietic cells (e.g., Epo, the interleukins; IL-1, IL-3, IL-6, IL-11, GM-CSF, G-CSF, M-CSF, SLF, LIF, TNF, lymphotoxin, flk2/flt3 ligand, kit-ligand, IGF-1 and γ-interferon, etc).

IV. Non-Therapeutic uses for Anti-flt2/flt3 Antibodies

The anti-flk2/flt3 antibodies are useful in diagnostic assays for flt2/flk3, e.g., detecting its expression in specific cells, tissues, or serum. The antibodies are labeled flk2/flt3 and/or are immobilized on an insoluble matrix. In one embodiment of a receptor binding assay, an antibody composition is immobilized on an insoluble matrix, the test sample is contacted with the immobilized antibody composition to adsorb the flk2/flt3, and then the immobilized family members are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

The antibodies also are useful for the affinity purification of flk2/flt3 from recombinant cell culture or natural sources. General affinity purification techniques are well known in the art, and any of these may be used for this purpose.

Suitable diagnostic assays for the anti-flk2/flt3 antibodies are well known per se. For example, competitive, sandwich and steric inhibition immunoassay techniques are useful. The competitive and sandwich methods employ a phase-separation step as an integral part of the method while steric inhibition assays are conducted in a single reaction mixture. Fundamentally, the same procedures are used for the assay of flk2/flt3 and for substances that bind flk2/flt3, although certain methods will be favored depending upon the molecular weight of the substance being assayed. Therefore, the substance to be tested is referred to herein as an analyte, irrespective of its status otherwise as an antigen or antibody, and proteins that bind to the analyte are denominated binding partners, whether they be antibodies, cell surface receptors, or antigens.

Analytical methods for flk2/flt3 or its antibodies all use one or more of the following reagents: labeled analyte analogue, immobilized analyte analogue, labeled binding partner, immobilized binding partner, and steric conjugates. The labeled reagents also are known as "tracers."

The label used (and this is also useful to label flk2/flt3 nucleic acid for use as a probe) is any detectable functionality that does not interfere with the binding of analyte and its binding partner. Numerous labels are known for use in immunoassay, examples including moieties that may be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, malate dehydrogenase, urease, peroxidase such as horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Those of ordinary skill in the art will know of other suitable labels that may be employed in accordance with the present invention. The binding of these labels to flk2/flt3, antibodies, or fragments thereof can be accomplished using standard techniques commonly known to those of ordinary skill in the art. For instance, coupling agents such as dialdehydes, carbodiimides, dimaleimides, bis-imidates, bis-diazotized benzidine, and the like may be used to tag the polypeptide with the above-described fluorescent, chemiluminescent, and enzyme labels. See, for example, U.S. Pat. No. 3,940,475 (fluorimetry) and U.S. Pat. No. 3,645,090 (enzymes); Hunter et al., *Nature,* 144:945 [1962];

David et al., *Biochemistry*, 13:1014–1021 [1974]; Pain et al., *J. Immunol. Methods*, 40:219–230 [1981]; Nygren, *J. Histochem. and Cytochem.*, 30:407–412 [1982]; O'Sullivan et al., *Methods in Enzymology*, ed. J. J. Langone and H. Van Vunakis, Vol. 73 (Academic Press, New York, N.Y. 1981), pp. 147–166; Kennedy et al., *Clin. Chim. Acta,* 70:1–31 [1976]; and Schurs et al., *Clin. Chim. Acta,* 81:1–40 [1977]. Coupling techniques mentioned in the lattermost reference are the glutaraldehyde method, the periodate method, the dimaleimide method, and the m-maleimidobenzyl-N-hydroxysuccinimide ester method.

In the practice of the present invention, enzyme labels are a preferred embodiment. No single enzyme is ideal for use as a label in every conceivable assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the assays of the present invention are alkaline phosphatase, HRP, beta-galactosidase, urease, glucose oxidase, glucoamylase, malate dehydrogenase, and glucose-6-phosphate dehydrogenase. Urease is among the more preferred enzyme labels, particularly because of chromogenic pH indicators that make its activity readily visible to the naked eye.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, flk2/flt3 or its immunologically active fragments are conjugated with a bifunctional organic bridge to an enzyme such as peroxidase. Conjugates are selected for use with anti-flk2/flt3 so that binding of the anti-flk2/flt3 inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of flk2/flt3 or flk2/flt3 antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-flk2/flt3 monoclonal antibody as one antibody and a polyclonal anti-flk2/flt3 antibody as the other is useful in testing samples for flk2/flt3 activity.

The agonist antibodies bind to and activate flk2/flt3 and are therefore useful diagnostic tools for further characterizing the biological activity of this receptor in vitro and/or in vivo. The agonist antibodies are also useful for diagnostic purposes. Similarly, the antibodies can be contacted with primitive hematopoietic cells and thereby lead to the proliferation and/or differentiation of mature blood cell lineages. This is useful where mature blood cells are required for scientific or therapeutic purposes or where the differentiation of cells is under investigation.

The foregoing are merely exemplary diagnostic assays for flk2/flt3 antibodies. Other methods now or hereafter developed for the determination of these analytes are included within the scope hereof, including the bioassays described above.

All citations throughout the specification and the references cited therein are hereby expressly incorporated by reference.

EXAMPLE 1

Production of Agonist Antibodies Against the Flk2/Flt3 Receptor

A. Cloning of Murine Flk2/Flt3 Receptor

The murine flk2/flt3 receptor was cloned by RT-PCR from RNA isolated from midgestation mouse fetal livers. Six sets of overlapping primers were designed to the murine flt-3 sequence disclosed by Rosnet et al. (*Oncogene,* 6:1641–1650 [1991]). These primers were designed to amplify three segments of the gene nucleotides 1–1307, 1308–1992, 1993–3096. The PCR products were then subcloned into pRK5.A. The sequence of the full-length flk2/flt3 gene was identical to the murine flt-3 gene sequence published by Rosnet et al., supra.

A flk2/flt3 extracellular domain (ECD) $IgG_1$ Fc fusion gene was constructed and fusion protein produced as previously described (Bennett et al., *J. Biol. Chem.,* 266:23060–23067 [1991]). The fusion protein was purified using protein A sepharose and the purified fusion protein was used for the generation of agonist antibodies against the flk2/flt3 receptor ECD.

B. Production of Polyclonal and Monoclonal Antibodies

Polyclonal antibodies were generated in New Zealand White rabbits against the flk2/flt3 fusion protein. 4 μg of fusion protein in 100 μL PBS was emulsified with 100 μL Freund's adjuvant (complete adjuvant for the primary injection and incomplete adjuvant for all boosts). For the primary immunization and the first boost, the protein was injected directly into the popliteal lymph nodes (Sigel et al., *Methods Enzymol.*, 93:3–12 [1983]). For subsequent boosts, the protein was injected into subcutaneous and intramuscular sites. 1.3 μg protein/kg body weight was injected every 3 weeks with bleeds taken 1 and 2 weeks following each boost. Baf-3 cells were transfected with the full length flk2/flt3 gene and used to determine the specificity of antibodies raised to the flk2/flt3-IgG fusion. Significant peak shifts were observed in flk2/flt3 expressing clones as compared to either pre-immune serum or vector alone transfectant controls. The polyclonal antiserum 579A was derived.

Anti-flk2/flt3 monoclonal antibodies were produced by hyperimmunizing BALB/c mice intraperitoneally with the flk2/flt3 extracellular domain (ECD)-human IgG, Fc fusion protein in RIBI adjuvant (RIBI ImmunoChem Research, Hamilton, Mont.) and fusing Syrian hamster splenocytes with the mouse myeloma cell line P3X63 Ag8 U.1 (Sanchez-Madrid et al., *Immunol. J.*, 130:309 [1983]). The antibodies were purified from ascites fluid using protein A-Sepharose (Repligen Corp., Cambridge, Mass.) and established affinity chromatography methods (Goding, *J. Immunol. Methods*, 20:241–253 [1978]). Flk2/flt3 specificity was assessed by flow cytometry analysis of BAF-3 cells transfected with the full-length receptor. The non-transfected parental line was used as a control. The 579A rabbit and polyclonal sera and IC2-514 monoclonal antibody were also demonstrated to immunoprecipitate the flk2/flt3 receptor from $S^{35}$-methionine labeled transfected cells lines.

Hamster anti-murine flk2/flt3 hybridomas IC2-514 and IC2-310 resulted from the screening. Hybridoma IC2-310 was deposited with the ATCC on Mar. 4, 1994 under accession number ATCC HB 11,557.

Agonist polyclonal and monoclonal antibodies were screened for, using the techniques disclosed below.

C. Assays for Agonistic Antibodies

Agonistic activity of the 579A polyclonal antisera and IC2-310 monoclonal antibody was determined using two assay systems: (a) a phosphotyrosine assay using the full length murine flk2/flt3 receptor expressed in the IL-3-dependent cell line BAF-3, and (b) a thymidine incorporation assay using the full-length receptor expressed in the IL-3 dependent cell line BAF-3. The BAF-3 cells were electroporated with the full-length flk2/flt3 receptor as previously described (Colosi et al., *J. Biol. Chem.*, 268:12617–12623 [1992]).

Tyrosine phosphorylation experiments were performed using flk2/flt3 receptor transfected into IL-3 dependent cells as previously described (Holmes et al., *Science*, 256:1205–1210 [1992]). Briefly, transfected Baf-3 cells (BAF-3T) or non-transfected BAF-3 cells (BAF-3) were starved of IL-3 and incubated with suspected agonist antibody (hybridoma supernatant polyclonal antisera diluted 1:20) or irrelevant control antibody for 30 minutes, lysed in IP lysis buffer (1% NP-40 , 1 mM EDTA, 200 mM NaCl, 50 mM Tris Hcl pH 8.0, 2 mM PMSF, 2.5 mM $Na_3 VO_4$) and immunoprecipitated with 579A polyclonal anti-sera. Immunoprecipitated lysates were separated on a 4–12% SDS-PAGE gradient gel, transferred to nitrocellulose and Western blotted using the antiphosphotyrosine antibody 4G10. Immunoblotting of the immunoprecipitated material using anti-phosphotyrosine antibodies demonstrated the phosphorylation of the flk2/flt3 receptor in response to both IC2-310 and 579A, with no phosphorylation of the 160 kD band observed for BAF-3 cells, untreated cells, or cells treated with an irrelevant control antibody. The molecular weight of the flk2/flt3 receptor probably reflects extensive glycosylation of the receptor as was predicted by sequence analysis (Matthews et al., supra). Similar molecular weight values for the full-length receptor have been obtained in other studies (Lyman et al., supra and Maroc et al., 1993, supra).

For the thymidine incorporation assay, 32D cells were starved of IL-3 for 24 hours and then stimulated with antibody overnight followed by an 8 hour pulse of 1 μCi [$^3$H] thymidine. Thymidine incorporation was then determined using a cell harvester. Both 579A and IC2-310 gave a significant stimulation of thymidine uptake in the transfected 32D cells. The specificity of these responses was demonstrated by the lack of response to irrelevant antibodies and to hamster IgG (FIG. 1). Following the discovery of IC2-310 agonist activity, the hybridoma supernatant was purified by protein-A affinity. The purified antibody retained activity at concentrations between 10–40 μg/ml. All subsequent in vitro assays routinely used 40 μg/ml.

The polyclonal antibody (579A) and IC2-310 monoclonal antibody were demonstrated in each of the above assays to be capable of activating the flk2/flt3 receptor.

EXAMPLE 2

Repopulation of the Hematopoietic System

This example established whether or not the flk2/flt3 receptor was expressed on hematopoietic stem cells capable of long-term engraftment of lethally irradiated hosts.

A. Isolation of Hematopoietic Stem Cell Populations

Hematopoietic stem cell populations were isolated from AA4[30] cells derived from midgestation fetal liver as previously described (Jordan et al., *Cell*, 61:953–963 [1990]). The AA4$^+$ cells were fractionated into Sca$^+$ and Sca$^-$ subpopulations using the ly6 A/E phycoerythrin conjugate (Pharmingen). The AA4 CD34$^+$ or CD34$^-$ populations were derived using an affinity purified rabbit anti-mouse CD34 (Baumhueter et al., *Science*, 262:436–438 [1993]). The purified IC2-514 monoclonal antibody discussed in Example 1 was conjugated to biotin or phycoerythrin for FACS analysis. The anti-mouse c-kit biotin conjugate was purchased from Pharmingen and all secondary and LIN cocktail antibodies were purchased from Caltag. Bone marrow hematopoietic stem cells were obtained from 8–12 week old C.57B/6 ly 5.1 or 5.2 mice. The mononuclear cell fraction was isolated by density gradient (Accudenz, Accurate Biochemicals) and stained with the LIN cocktail antibodies as previously described (Jordan et al, supra). LIN stained cells were removed via magnetic bead depletion (Dynal, Inc., Ploemacher et al., *Blood*, 74:2755–2763 [1989]) and the Lin$^{lo}$ population was stained using the appropriate antibodies. Stained cells were selected by propidium iodine (1 μg/ml) exclusion and separated on an Elite flow cytometer (Coulter Electronics, Haileah, Fla.).

B. Competitive Repopulation

The competitive repopulation technique employed in the following experiment allows for comparison of the stem cell content of each of the derived populations. Competitive repopulation determines the proliferative capacity of two populations of donor hematopoietic cells (Harrison et al., *Hematol. E.*, 21:206–219 [1993]). In this instance, one million bone marrow cells were used as the competitor and the stem cell content of the potential stem cell population, for example, AA4⁺Sca⁺flk-2⁺ was measured relative to the competitor population.

The stem cell equivalents (SCE) per 10,000 cells were determined using competitive repopulation analysis of genetically marked fetal liver or bone marrow in C57BL/6 mice allelic at the Ly 5 locus, designated Ly 5.1 and Ly 5.2. Ly 5.1 expression in the Ly 5.2 mice was determined at selected intervals post engraftment.

Stem cell populations were isolated from young adult C57B1/6 Ly 5.1 mice. Young adult male C57B/6 Ly 5.2 mice were obtained from NCI and used as recipients. A minimum of five animals was used per experimental group. Whole body irradiation (1100 cGy, 190 cGy/min) was administered as a single dose from a C137 source. In general, one million bone marrow cells from the 5.2 mice were used as competitors and the stem cell content of $1 \times 10^4$ ly 5.1 cells of the potential stem cell population, e.g., AA4⁺ Sca⁺flk-2⁻ was measured relative to the competitor population. Cells were administered via tail vein injection and peripheral blood samples (50–100 μl) were obtained via the retro-orbital sinus 4 weeks, 12 weeks and 6 months post-reconstitution. The percentage of ly 5.1 donor cells was determined by staining with biotin conjugated ly 5.2 monoclonal (A20.1.7). To confirm repopulation by the donor ly 5.1 cells in all lineages, peripheral blood cells and the bone marrow mononuclear fraction were stained with the following antibodies; B220 (β-cell lineages), CD4/8 (T cell lineages), Gr-1/Mac-1 (myeloid lineages).

The number of stem cells in each sample (stem cell equivalents, SCE) were determined as described by Kiefer et al., (*Blood*, 78:2577–2582 [1991]). The stem cell content of the bone marrow was estimated at one stem cell per $10^5$ total bone marrow cells (Harrison et al., supra). Therefore, the $1 \times 10^6$ bone marrow cells used as a competitor contained 10 stem cells. This means the contribution of the ly 5.1 stem cell population being tested is therefore defined by the equation:

$$x \div (10+x) = \text{mean fraction of \% ly 5.1 repopulation}$$

$$x = SCE$$

The results are shown in Table 1. All the lineages were reconstituted by donor 5.1 cells. The results from the AA4⁺ kit⁺ flk-2⁺/⁻ isolations represent an 8 week time point.

the Sca-1 antigen (ly6A/E). The AA4⁺ Sca⁺ population contains all the totipotent stem cell activity (Matthews et al., supra). Experiments using the CD34 polyclonal antibody demonstrated that 60% of the AA4⁺ population are CD34 positive (FIG. 1). Furthermore, repopulation studies showed all the stem cell activity to reside in the AA4⁺ CD34⁺ fraction and that the AA4⁺ CD34⁻ population did not repopulate (Table 1). It is of further interest to note that all AA4⁺ CD34⁺ cells are positive for c-kit expression (FIG. 2) and that all AA4⁺ Sca⁺ cells are also CD34 positive. It was also demonstrated that the c-kit positive fraction of the AA4⁺ population contained all stem cell activity. The AA4⁺ Sca⁺, AA4⁺ CD34⁺, and the AA4⁺ kit⁺ stem cell populations were used to investigate stem cell expression of the flk2/flt3 receptor (FIG. 2). Repopulation studies demonstrated that flk2/flt3 receptor can be expressed on stem cells but that both flk2/flt3 positive and negative stem cell fractions give rise to long term reconstitution (Table 1). In experiments using bone marrow as the source for stem cells, the mononuclear fraction was segregated into a Lin$^{lo}$ population by immunomagnetic bead separation using the Lin cocktail of antibodies to mature hematopoietic cell types (Ploemacher et al., *Blood*, 74:2755–2763 [1989]). The Lin$^{lo}$ mononuclear cells were fractionated into Lin$^{lo}$ CD34⁺ and Lin$^{lo}$ Sca⁺ stem cell fractions (FIG. 2). In accordance with the fetal liver populations, these bone marrow stem cell populations gave both flk2/flt3 positive or flk2/flt3 negative sub-populations. Both of is these sub-populations gave rise to long term repopulation (Table 1).

The above experiments demonstrate the high stem cell content of the AA4⁺ CD34⁺ kit⁺ and AA4$^{30}$ Sca$^{30}$ flk-2$^{31}$ populations. Furthermore, they indicate a general trend suggesting that the flk2/flt3 negative cell populations have a greater stem cell content when compared to the relevant flk2/flt3 positive population (Table 1). It is noteworthy that in the marrow there are very few Lin$^{lo}$ Sca⁺ flk-2⁻ cells, most of the Lin$^{lo}$ Sca⁺ population being flk2/flt3 positive (FIG. 2). The fractionation of Lin$^{lo}$ mononuclear cells from the bone marrow into flk-2⁺ and flk-2⁻ cells demonstrated that the Lin$^{lo}$ flk-2⁺ cells were more potent at short term repopulation of the irradiated host (3.47 versus 1.25 stem cell equivalents per 10,000 cells). Indeed, repopulation from the Lin$^{lo}$ flk-2⁺ cells was minimal after 12 weeks. This suggests that the Lin$^{lo}$ flk-2⁺ population is comprised of more committed progenitors than its flk-2⁻ counterpart.

TABLE 1

|  | 4 WEEKS | | 12 WEEKS | | 24 WEEKS | |
| --- | --- | --- | --- | --- | --- | --- |
|  | % 5.1 | SCE | % 5.1 | SCE | % 5.1 | SCE |
| AA4⁺ Sca⁺ Flk-2⁺ | 72 ± 3 | 13 | 83 ± 4 | 24 | 90 ± 2 | 45 |
| AA4⁺ Sca⁺ Flk-2 (⁻) | 68 ± 3 | 11 | 89 ± 5 | 41 | 92 ± 2 | 57 |
| AA4⁺ CD34⁺ Flk-2 ⁺ | 41 ± 12 | 4 | 66 ± 10 | 10 | 68 ± 9 | 11 |
| AA4⁺ CD34⁺ Flk-2 (⁻) | 58 ± 18 | 7 | 77 ± 9 | 17 | 84 ± 4 | 26 |
| AA4⁺ Kit⁺ Flk-2⁺ | 61 ± 6 | 16 | 71 ± 5 | 24 | — | — |
| AA4⁺ Kit⁺ Flk-2 (⁻) | 27 ± 7 | 4 | 46 ± 10 | 9 | — | — |
| AA4⁺ CD34⁺ Kit⁺ | 75 ± 4 | 30 | 84 ± 5 | 39 | 70 ± 3 | 23 |
| AA4⁺ CD34⁺ | 42 | 7 | 51 ± 14 | 10 | 49 ± 24 | 9 |
| AA4⁺ Kit⁺ CD34 (⁻) | 2 ± 2 | 0 | 23 ± 6 | 3 | 4 ± 3 | 0 |
| LIN¹⁰ CD34⁺ Flk-2⁺ | 51 | 10 | 44 ± 25 | 8 | 53 ± 22 | 11 |
| LIN¹⁰ Sca⁺ Flk-2⁺ | 50 | 10 | 40 ± 6 | 7 | 25 ± 1 | 3 |
| LIN¹⁰ Sca⁺ Flk-2 (⁻) | 57 | 13 | 53 ± 10 | 11 | 67 ± 12 | 20 |

In the fetal liver, the AA4.1 antibody (AA4) delineates a population of one percent of the cells in which all the totipotent stem cell activity resides (Jordan et al., supra). The AA4⁺ population can be further enriched using antibodies to These reconstitution experiments of lethally irradiated mice clearly demonstrate that the flk2/flt3 receptor tyrosine kinase is expressed on stem cell populations, but quite clearly, not all stem cells express flk2/flt3. This finding was confirmed in all the different fetal liver and bone marrow stem cell populations isolated. Using competitive repopulation, it was demonstrated that flk-2 positive stem cell fractions have significantly less repopulating capacity than their relative flk-2 negative counterparts.

The most widely used marker for the study of human hematopoietic cells is cell surface expression of CD34. Various functional assays have demonstrated that the CD34 positive sub-population from human marrow contains virtually all primitive hematopoietic cells (Andrews et al., *Med. JE.*, 16:1721 [1989]; Berenson et al., *Invest. JC.*, 81:951–955 [1988]; Civin et al., *Immunol. J.*, 133:157–165 [1984]; and Sutherland et al., *Blood*, 74:1563–1569 [1989]). The monospecific polyclonal antibody to murine CD34 clearly demonstrated that in accordance with the human homologue, the stem cell activity in murine hematopoiesis is confined to the CD34$^+$ fraction. Therefore, the phenotype of the murine hematopoietic stem cell from the fetal liver is AA4$^+$ Lin$^{lo}$ Sca$^+$ CD34$^+$ kit$^+$ flk-2$^{+/-}$. From the bone marrow, the phenotype of the stem cell is Lin$^{lo}$ Sca$^+$ kit$^+$ CD34$^+$ flk-2$^{+/-}$.

EXAMPLE 3

Cell Cycle Analysis of Flk2/Flt3 Expression

Cell cycle analysis of hematopoietic stem cell populations has previously indicated that stem cell populations are heterogeneous in relation to cell cycle status (Fleming et al., *Biol. JC.*, 122:897–902 [1993] and Suda et al., *Physiol., JC.*, 17:308 [1983]). Furthermore, enhanced repopulation has been attributed to those stem cells in the $G_0/G_1$ phase compared to the actively proliferating $S/G_2/M$ subset (Fleming et al., supra). If flk2/flt3 expression on stem cells represents a potentially more committed stem cell population, exhibiting decreased repopulation capacity, this may be reflected in the cell cycle status. Additionally, it has been suggested that flk2/flt3 RNA expression is correlated with cycling stem cells (Orlic et al., supra and Visser et al., supra). Therefore, the cell cycle status of the fetal liver stem cell population AA4$^+$ Sca$^+$ was determined with respect to flk2/flt3 expression (FIG. 3). A two-step acridine orange staining technique was employed to differentiate $G_0$ from $G_1$ phase cells. When coupled with conventional cell cycle analysis of the DNA content histogram, this method allows for the simultaneous analysis of the $G_0$, $G_1$, S and $G_2$M cell cycle phase compartments of any cell population.

Two-step acridine orange staining was performed as detailed previously (Darzynkiewicz and Kapuscinski, Flow Cytometry and Sorting, 2nd edition, Wiley-Liss, 291–314; and Baumhueter et al., *Science*, 262:436–438 [1993]). Briefly, cells which had been sorted following dual-parameter immunofluorescence staining were centrifuged (400×5 min) and resuspended in RPMI 1640 cell culture medium with 10% fetal bovine serum at a final concentration of 10$^6$/ml. To 0.3 ml of this cell suspension, a solution consisting of 0.45 ml of 0.1% Triton X-100 in 0.15N NaCl and 0.08N Hcl was added and the mixture incubated for 45 seconds on ice. To this solution, 1.8 ml of a solution consisting of 12 μm acridine orange (Polysciences, Inc.) in 0.2M Na$_2$HPO$_4$, 0.1M citric acid, 10$^{-3}$M Na-EDTA and 0.15M NaCl was added and the sample immediately analyzed by flow cytometry. Red fluorescence (RNA) and green fluorescence (DNA content) were simultaneously collected by the addition of a 560 nm dichroic long-pass filter coupled with a 525 +/-15 nm bandpass filter (green fluorescence) and a 630 nm long-pass filter (red fluorescence).

The $G_0$ sub-population was defined on the basis of the red fluorescence of peripheral blood mononuclear cells (PBMC) stained in parallel to the previously sorted samples. A cursor was placed at the position corresponding to the red fluorescence intensity of 97% of PBMC, with cells having higher RNA contents above this position classified as cycling (i.e. $G_1$, S, $G_2$M) populations, and those at or below the cursor classified as $G_0$. Enumeration of the proportions of cycling cells was performed by conventional cell cycle analysis using the algorithm of Dean and Jett, 1974; available in the Multicycle software (Phoenix Flow Systems, San Diego, Calif.).

It was demonstrated that the major difference between the two sub-populations (AA4$^+$ Sca$^+$ flk-2$^+$ and AA4$^+$ Sca$^+$ flk-2$^-$) was the greatly increased percentage of cells residing in $G_0$ in the AA4$^+$ Sca$^+$ flk-2$^-$ population (FIG. 3). The percentage of cells in $S/G_2/M$ clearly indicated that these fetal liver stem cell populations contain many actively proliferating cells.

Cell cycle analysis of the AA4$^+$ kit$^+$ stem cell populations demonstrated a much lower percentage of cells in $G_0$ when compared to the AA4$^+$ Sca$^+$ flk-2$^-$ population. However, little difference was found between the AA4$^+$ kit$^+$ flk-2$^+$ ($G_0$-12%, $G_1$-39%, $G_2$/M-8%) and the AA4$^+$ kit$^+$ flk-2$^-$ ($G_0$-7%, $G_1$-47%, S-41%, $G_2$/M-5%) populations.

These data indicate that the flk2/flt3 receptor is expressed by a subset of hematopoietic stem cells destined to differentiate to more committed progenitor cells. This hypothesis gains support from studies that have demonstrated decreased radioprotective capacity in cycling stem cells (Fleming et al., *Biol. JC.*, 122:897–902 [1993]), and from the expression of flk2/flt3 mRNA in stem cell fractions believed to be actively cycling (Orlic et al., *Blood*, 82:762–770 [1993]; and Visser et al., *Cells S.*, 11:49–55 [1993]).

EXAMPLE 4

Hematopoietic Assays of the Flk2/Flt3 Agonist Monoclonal Antibody

A. Dexter Culture Assay System

To assist in the evaluation of the biological function of the IC2-310 agonist antibody a Dexter culture assay system was developed using immortalized stromal cell lines from the fetal liver.

Fetal liver stromal cells were isolated by infecting primary cultures of fetal stroma with the recombinant retrovirus as previously described (Larsson et al., *Immunol. D.*, 1:279–293 [1991]). Viral stocks of recombinant retroviruses pZipSvtsA58 were prepared from previously characterized virus producing ψ2 cell lines (Cepko et al., *Cell*, 37:1053–1062 [1984]; and Sharp et al., is *Biol. MC.*, 9:1672–1681 [1989]. One of the resultant stromal cell lines designated 7-4 was used in these experiments.

The following stromal cell/stem cell co-culture assay was performed. Hematopoietic stem cell populations were seeded at 10$^4$ cells/ml on the fetal liver stromal line 7-4 in DMEM/F12 media supplemented with 10% FCS. Co-cultures were incubated at 37° C. for 7 days. The stem cell content was determined by competitive repopulation analysis prior to and after 7 days of coculture. The results obtained from each in vitro assay system were confirmed in a minimum of three independent experiments. Growth factors were used at the following concentrations: KL-50 ng/ml; IL-3-1 ng/ml (Genzyme); GM-CSF- 0.2 ng/ml (R & D Systems); PDGF B/B-2 ng/ml; and bFGF 2.5 ng/ml (Boehringer Mannheim, USA, Indianapolis, Ind.). Control wells were media alone or media spilled with hamster Ig-G.

After 7 days of coculture the resulting cell populations could only sustain short-term repopulation of the irradiated host as evidenced by contribution of donor co-cultivated cells at 4 weeks post-engraftment. However, after this early time point no further contribution from the co-cultivated cells was observed.

Cocultivation upon the 7-4 stroma gave rise to dramatic expansion in cell number. See Table 2 below.

TABLE 2

| CELL POPULATION | CONTROL | 310 | KL | KL + 310 |
|---|---|---|---|---|
| AA4+ Kit+ Flk-2+ | 33 ± 14 | 52 ± 2 | 210 ± 18 | 276 ± 12 |
| AA4+ Kit+ Flk-2 (−) | 32 ± 3 | 28 ± 1 | 71 ± 12 | 84 ± 5 |
| AA4+ SCA+ | 8 ± 0.71 | 31 ± 2.1 | 120 ± 14 | 180 ± 13 |
| AA4+ SCA (−) | 6 ± 0.71 | 6 ± 0.84 | 13 ± 0.35 | 12 ± 0.35 |
| AA4+ CD34+ Kit+ | 12 ± 2.6 | 22 ± 2.3 | 95 ± 6.1 | 129 ± 7 |
| AA4+ CD34+ Flk-2+ | 25 ± 5 | 52 ± 11 | | |
| AA4+ CD34+ Flk-2 (−) | 12 ± 3 | 14 ± 5 | | |
| LIN$^{10}$ CD34+ Flk-2+ | 52 ± 7 | 173 ± 38 | | |

Lineage analysis of the resultant cell populations was performed using flow cytometric analysis and Wright Geisha staining of cytopsin material. These analyses demonstrated the presence of immature progenitor, myeloid and lymphoid cells (see Table 3 below).

TABLE 3

CYTOPSIN ANALYSIS

| AA4+ Sca+ | % Blasts | % lg MNC | % Myeloid | % Lymphoid |
|---|---|---|---|---|
| Media alone | 28 | 47 | 13 | 12 |
| IC2-310 | 10 | 52 | 30 | 8 |
| IC2-310/KL | 15 | 35 | 47 | 3 |
| IC2-310/GMCSF | 12 | 31 | 52 | 2 |
| IC2-310/KL/GMCSF | 3 | 23 | 70 | 4 |

FACS ANALYSIS

| AA4+ Sca+ | % MAC-1* | % Gr-1* | % β220* | % CD4/CD8+ |
|---|---|---|---|---|
| Control | 65 | 64 | 11 | 36 |
| 310 | 76 | 63 | 22 | 46 |

Many cells maintained the expression of Sca, flk2/flt3, c-kit and CD34. The multilineage potential of this hematopoietic micro-environment was further underscored in the following experiment. Hematopoietic cells were harvested from the stem cell/stromal cell cocultivation after 7 days and stained for FACS analysis using MAC-1 antibody (macrophages), GR-1 (granulocytes), β220 (β cells), CD4/8 (T cell markers). These data are presented from one representative experiment. The experiments were repeated a maximum of three times. The results are shown in Table 3.

This was confirmed by cytospin analysis which identified a variety of hematopoietic cell types including those of the myeloid and lymphoid series. Cytopsin differentials from the AA4+ CD34+ kit+ stem cell populations after cocultivation with stromal cell line 7-4 for 7 days were co-cultivated in the presence of the growth factors indicated. Blasts are cells of immature phenotype containing precursors to many lineages. Large mononuclear cells (lg MNC) are cells of intermediate size and differentiation containing many precursor cells of both lymphoid and myeloid lineages. Myeloid cells are cells of mature myeloid images. Lymphold cells are cells displaying lymphocyte or plasma cell characteristics. See Table 3.

Stem cells plated in the presence of the IC2-310 agonist antibody gave rise to a greater proliferative event than seen when plated upon 7-4 alone. However, IC2-310 did not induce proliferation of the non-stem cell populations such as AA4+ Sca−. Furthermore, IC2-310 had no effect on the non-flk2/flt3 expressing stem cell populations (Table 2). FACS analysis of these cells again demonstrated the presence of several potential lineages (Table 3). As with cells grown on 7-4 alone, the IC2-310 stimulated cells were only capable of repopulating in the short term. The proliferative event enhanced by the IC2-310 antibody was greatly increased in combination with KL (Table 2). Cytospin analysis of the cocultivated cells demonstrated a significant drop in the percentage of blast cells with a concomitant increase in the percentage of cells from the myeloid lineages including myeloblasts, myelocytes, promyelocytes or metamyelocytes (Table 3). Taken together, these data demonstrate the overall proliferation resulting from stimulation of the flk2/flt3 receptor. Furthermore, they illustrate that in the context of cocultivation on the 7-4 stromal cell line, this proliferative event is accompanied by differentiation to more mature hematopoietic phenotypes.

It is clear that activation of the flk2/flt3 receptor promotes the proliferation and differentiation of hematopoietic stem cells when they are cocultivated with stroma. This proliferation is most clearly evidenced by the increases in both cell number and colony forming cells obtained upon activation of stem cells with the IC2-310 agonist antibody. Conversely, the agonist antibody has little effect on non-stem cell populations.

Proliferation of the hematopoietic system by IC2-310 appears to be restricted to stem cell populations and gives rise to an expanded population or more mature hematopoietic phenotypes.

D. Effect of IC2-310 Monoclonal Antibody on Methyl Cellulose Colony Formation

Hematopoietic colony assays were performed to determine the effects of the IC2-310 antibody on the colony forming potential of primitive hematopoietic populations. The methylcellulose assays were performed in the presence of WEHI conditioned media supplemented with KL in order to test the myeloid potential of the input cell, or alternatively, in the presence of IL-7 and KL to test the β-lymphoid potential (McNiece et al., *Immunol. J.,* 146:3785–3790 [1991]). Standard myeloid methylcellulose colony assays were performed using complete methylcellulose medium (Stem Cell Technologies, Inc., #M3430) with the addition of 50 ng/ml kit ligand, KL (R & D Systems, Minneapolis, Minn.). Colonies were counted after 10 days in culture; only colonies of greater than 50 cells were scored. Lymphoid colonies were produced using base methylcellulose (Stem Cell Technologies) with 50 ng/ml kit ligand and 50 ng/ml murine IL-7 (R & D Systems, Minneapolis, Minn.), see McNiece et al., supra. Cytospin analysis of the resultant colonies was performed as previously described (Testa and Molineux, Hematopoiesis: Oxford IRL Press).

Figure 4:
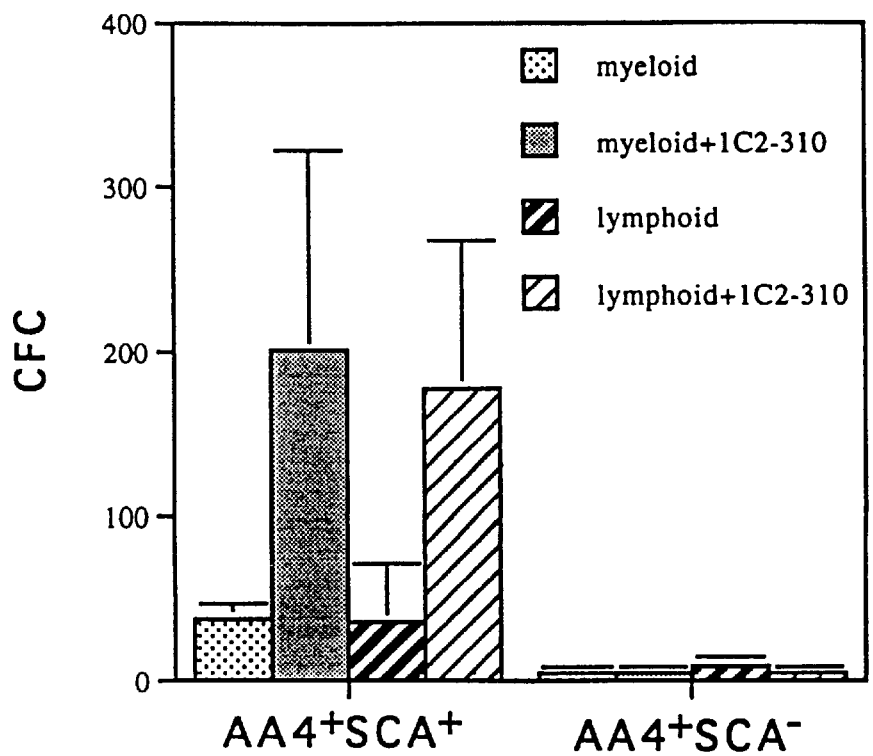
FIG. 4 depicts the effect of IC2-310 on methyl cellulose colony formation. Hematopoietic cells were seeded into methylcellulose after being cocultivated on the 7-4 fetal liver stromal line for 7 days in the presence or absence of IC2-310 agonist antibody. The methylcellulose cultures were established under conditions forming either myeloid or lymphoid colonies. Colonies were then stored for CFC after 10 days in culture. Assays were performed in triplicate and repeated in three separate experiments.
Figure 2A:
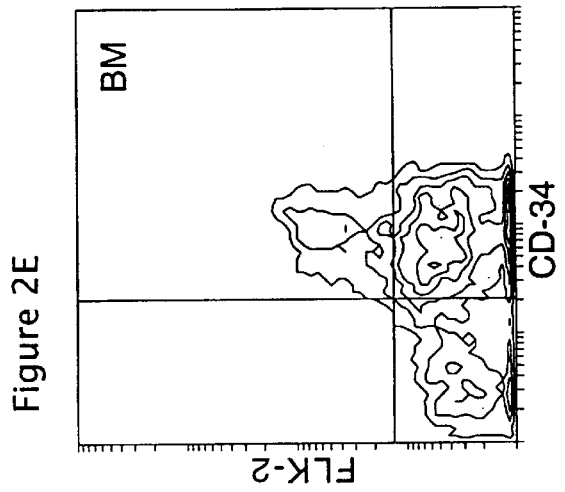
FIGS. 2A–F show fractionation of fetal liver and bone marrow stem cell populations.
Figure 2B:
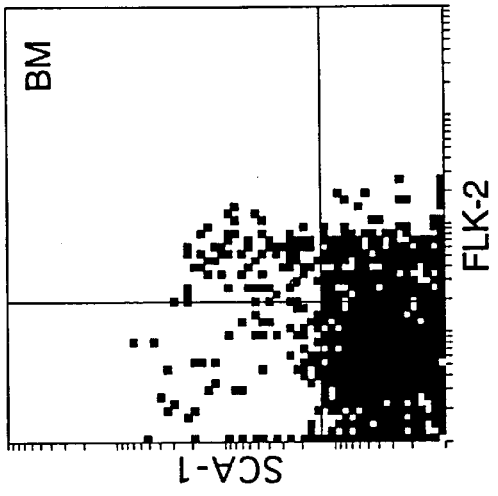
Figure 2C:
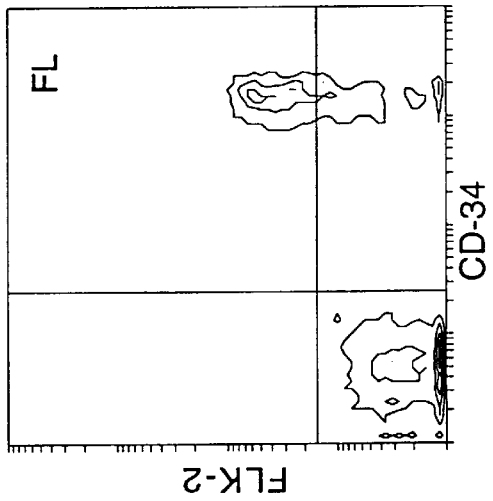
Figure 2D:
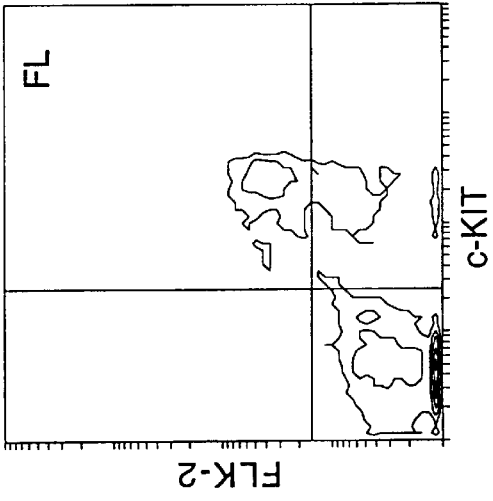
Figure 2E:
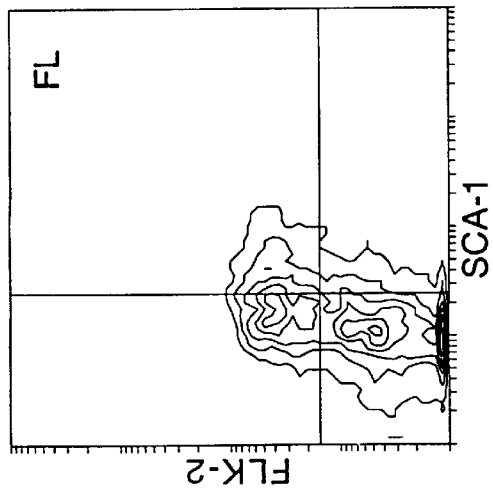
Figure 2F:
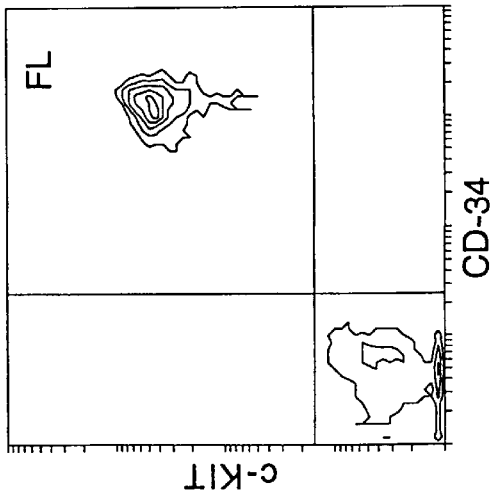
Figure 3A:
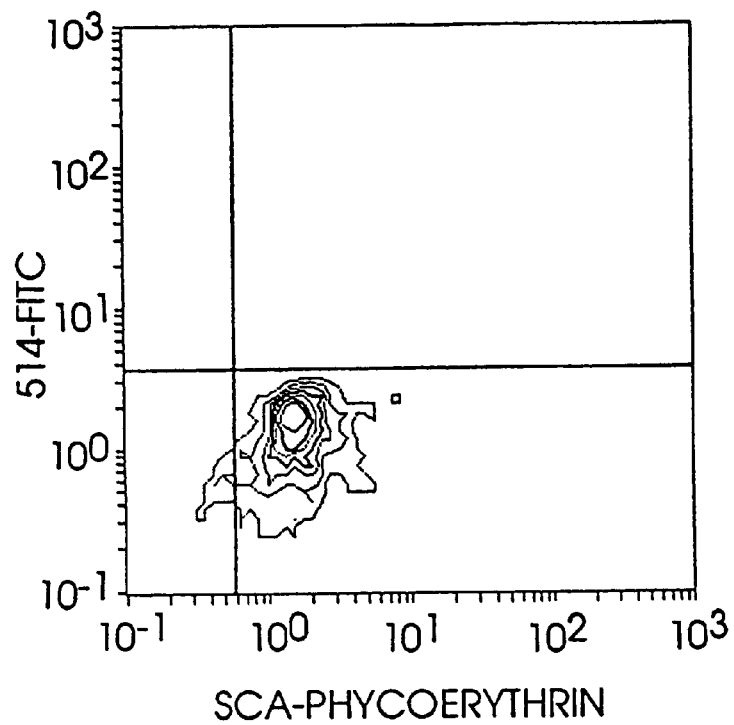
FIGS. 3A–D depict dual-parameter fluorescence histograms of AA4$^+$ SCA$^+$ flk-2$^-$ (FIG. 3A) and AA4$^+$ SCA$^+$ flk-2$^+$ enriched (FIG. 3B) populations following cell sorting.
Figure 3B:
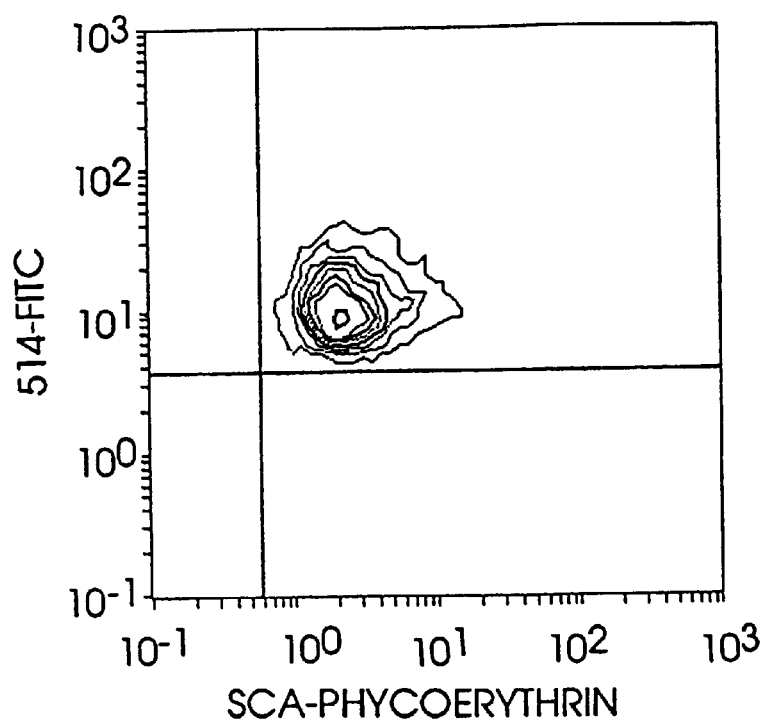
Figure 3C:
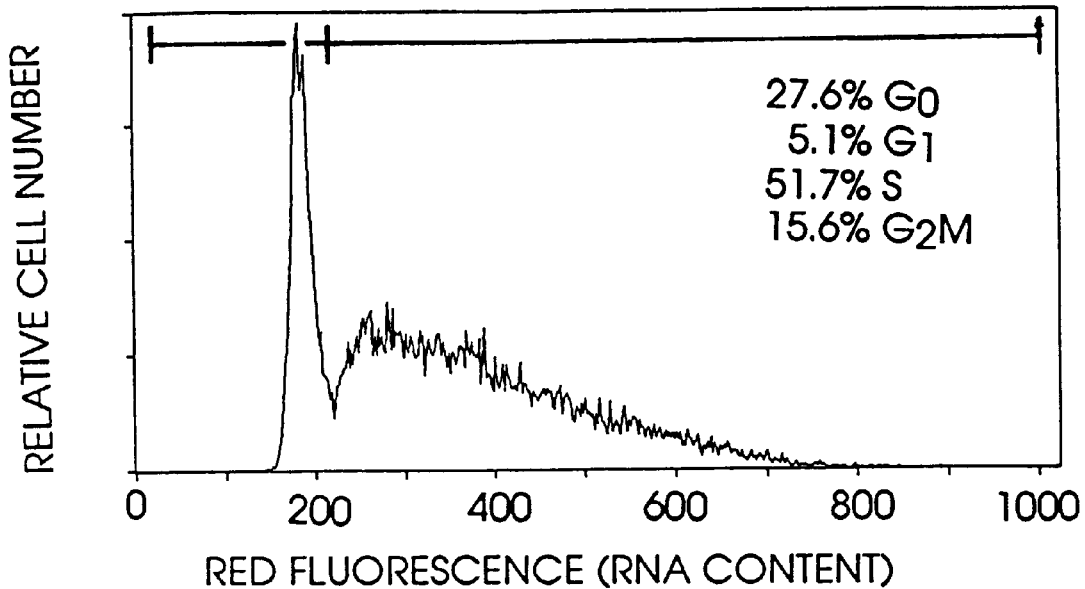
Figure 3D:
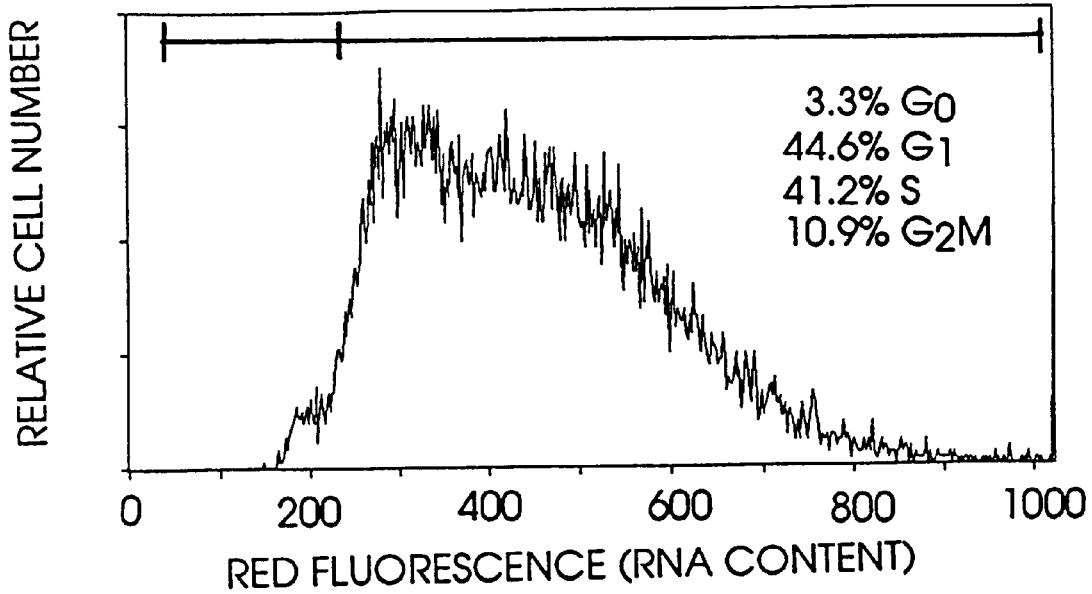

Hematopoietic stem cell populations plated onto 7-4 cells and then removed after 7 days were capable of forming both myeloid colony forming cells (CFC) and lymphoid CFC. When the cocultivation on 7-4 was performed in the presence of IC2-310 agonist antibody there was an approximate 5 fold increase in myeloid CFC and a 12 fold increase in lymphoid CFC (FIG. 4). Cytospin data revealed the myeloid colonies to be of mixed lineage but principally they represented the granulocyte/macrophage subset. Analysis of the colonies produced in the presence of IL-7 and KL demonstrated a B220⁺ IgM⁻ phenotype. Most of these cells also stained for the S7 marker which is considered to stain β lineage cells before the pre-β stage (Hardy et al., *J. Exp. Med.*, 173:1213–1225 [1991]). Once again, the proliferative effect of IC2-310 was restricted to the stem cell population. No effect was seen on the AA4⁺ Sca⁻ cell population which does not contain stem cells (FIG. 4).

These results support the observations that the IC2-310 antibody is only capable of stimulating proliferation of the most primitive hematopoietic cell populations.

Deposit of Materials

The following culture has been deposited with the American Type Culture Collection, 12301 Parklawn Drive, Rockville, Md., USA (ATCC):

| Hybridoma | ATCC No. | Deposit Date |
|---|---|---|
| Anti-FLK2/FLT3 | ATCC HB 11,557 | March 4, 1994 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty, and subject to an agreement between Genentech, Inc. and ATCC, which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the culture deposited, since the deposited embodiment is intended as a single illustration of one aspect of the invention and any culture that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

We claim:

1. A method for enhancing proliferation or differentiation of hematopoietic cells comprising contacting the hematopoietic cells with an effective amount of an agonist antibody which binds to the extracellular domain of flk2/flt3 and activates the tyrosine kinase domain of flk2/flt3.

2. The method of claim 1 wherein the agonist antibody is a monoclonal antibody.

3. The method of claim 1 wherein the agonist antibody causes the differentiation or proliferation of myeloid and lymphoid blood cell lineages.

4. The method of claim 1 further comprising contacting the hematopoietic cells with steel factor (SLF).

5. A method for enhancing repopulation of mature blood cell lineages in a mammal comprising administering to the mammal a therapeutically effective amount of an agonist antibody which binds to the extracellular domain of flk2/flt3 and activates the tyrosine kinase domain of flk2/flt3.

6. The method of claim 5 wherein the mammal has undergone chemotherapy, radiation therapy, or bone marrow transplantation therapy, or has suffered a decrease in blood cell lineages as a consequence of having suffered hemorrhage or disease.

7. The method of claim 3 wherein the agonist antibody causes a synergistic increase in the proliferation or differentiation of primitive hematopoietic cells in combination with steel factor (SLF).

8. The method of claim 1 which enhances the proliferation or differentiation of primitive hematopoietic cells.

9. The method of claim 1 wherein the agonist antibody has the biological characteristics of the monoclonal antibody produced by the hybridoma cell line deposited under American Type Culture Collection Accession Number ATCC HB 11,557.

10. The method of claim 1 wherein the agonist antibody binds to the epitope to which the monoclonal antibody produced by the hybridoma cell line deposited under American Type Culture Collection Accession Number ATCC HB 11,557 binds.

11. The method of claim 1 wherein the agonist antibody gives rise to an expansion in cell number of AA4$^+$Kit$^+$Flk- $2^+$, $AA4^+Sca^+$, $AA4^+CD34^+Kit^+$, $AA4^+CD34^+Flk-2^+$, and $LIN^{lo}CD34^+Flk-2^+$ cell populations in vitro.

12. The method of claim 1 wherein the agonist antibody does not give rise to an expansion in cell number of an $AA4^+Sca^-$ cell population in vitro.

13. The method of claim 1 wherein the agonist antibody enhances proliferation and differentiation of hematopoietic stem cells destined to differentiate to more committed progenitor cells.

14. The method of claim 1 wherein the agonist antibody comprises complementarity determining region (CDR) residues of a non-human antibody and framework region residues of a human antibody.

15. The method of claim 1 further comprising contacting the hematopoietic cells with a cytokine capable of enhancing the proliferation or differentiation of hematopoietic cells.

16. The method of claim 15 wherein the cytokine is selected from the group consisting of Epo, IL-1, IL-1α, IL-2, IL-3, IL-4, IL-5, IL-6, IL-7, IL-8, IL-9, IL-11, IL-12, GM-CSF, G-CSF, M-CSF, SLF, LIF, TNF, lymphotoxin, flk2/flt3 ligand, kit-ligand, IGF-1 and γ-interferon.

17. The method of claim 1 wherein the hematopoietic cells are in a mammal.

18. The method of claim 17 wherein the mammal is a human.

19. The method of claim 5 wherein the agonist antibody enhances proliferation and differentiation of myeloid and lymphoid blood cell lineages.

20. The method of claim 19 wherein the agonist antibody causes a synergistic increase in the proliferation or differentiation of primitive hematopoietic cells in combination with steel factor (SLF).

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 3521 bases
      (B) TYPE: nucleic acid
      (C) STRANDEDNESS: single
      (D) TOPOLOGY: linear (xi) SEQUENCE DESCRIPTION: SEQ ID NO:1:

```
GCCACCTGCA GCCCGGGGCG CGCCGCTGGG ACCGCATCAC AGGCTGGGCC              50

GGCGGCCTGG CTACCGCGCG CTCCGGAGGC CATGCGGGCG TTGGCGCAGC             100

GCAGCGACCG GCGGCTGCTG CTGCTTGTTG TTTTGTCAGT AATGATTCTT             150

GAGACCGTTA CAAACCAAGA CCTGCCTGTG ATCAAGTGTG TTTTAATCAG             200

TCATGAGAAC AATGGCTCAT CAGCGGGAAA GCCATCATCG TACCGAATGG             250

TGCGAGGATC CCCAGAAGAC CTCCAGTGTA CCCCGAGGCG CCAGAGTGAA             300

GGGACGGTAT ATGAAGCGGC CACCGTGGAG GTGGCCGAGT CTGGGTCCAT             350

CACCCTGCAA GTGCAGCTCG CCACCCCAGG GGACCTTTCC TGCCTCTGGG             400

TCTTTAAGCA CAGCTCCCTG GGCTGCCAGC CGCACTTTGA TTTACAAAAC             450

AGAGGAATCG TTTCCATGGC CATCTTGAAC GTGACAGAGA CCCAGGCAGG             500
```

```
AGAATACCTA CTCCATATTC AGAGCGAAGC CGCCAACTAC ACAGTACTGT        550

TCACAGTGAA TGTAAGAGAT ACACAGCTGT ATGTGCTAAG GAGACCTTAC        600

TTTAGGAAGA TGGAAAACCA GGATGCACTG CTCTGCATCT CCGAGGGTGT        650

TCCGGAGCCC ACTGTGGAGT GGGTGCTCTG CAGCTCCCAC AGGGAAAGCT        700

GTAAAGAAGA AGGCCCTGCT GTTGTCAGAA AGGAGGAAAA GGTACTTCAT        750

GAGTTGTTCG GAACAGACAT CAGATGCTGT GCTAGAAATG CACTGGGCCG        800

CGAATCGACC AAGCTGTTCA CCATAGATCT AAACCAGGCT CCTCAGAGCA        850

CACTGCCCCA GTTATTCCTG AAAGTGGGGG AACCCTTGTG GATCAGGTGT        900

AAGGCCATCC ATGTGAACCA TGGATTCGGG CTCACCTGGG AGCTGGAAGA        950

CAAAGCCCTG GAGGAGGGCA GCTACTTTGA GATGAGTACC TACTCCACAA       1000

ACAGGACCAT GATTCGGATT CTCTTGGCCT TTGTGTCTTC CGTGGGAAGG       1050

AACGACACCG GATATTACAC CTGCTCTTCC TCAAAGCACC CCAGCCAGTC       1100

AGCGTTGGTG ACCATCCTAG AAAAAGGGTT TATAAACGCT ACCAGCTCGC       1150

AAGAAGAGTA TGAAATTGAC CCGTACGAAA AGTTCTGCTT CTCAGTCAGG       1200

TTTAAAGCGT ACCCACGAAT CCGATGCACG TGGATCTTCT CTCAAGCCTC       1250

ATTTCCTTGT GAACAGAGAG GCCTGGAGGA TGGGTACAGC ATATCTAAAT       1300

TTTGCGATCA TAAGAACAAG CCAGGAGAGT ACATATTCTA TGCAGAAAAT       1350

GATGACGCCC AGTTCACCAA AATGTTCACG CTGAATATAA GAAAGAAACC       1400

TCAAGTGCTA GCAAATGCCT CAGCCAGCCA GGCGTCCTGT TCCTCTGATG       1450

GCTACCCGCT ACCCTCTTGG ACCTGGAAGA AGTGTTCGGA CAAATCTCCC       1500

AATTGCACGG AGGAAATCCC AGAAGGAGTT TGGAATAAAA AGGCTAACAG       1550

AAAAGTGTTT GGCCAGTGGG TGTCGAGCAG TACTCTAAAT ATGAGTGAGG       1600

CCGGGAAAGG GCTTCTGGTC AAATGCTGTG CGTACAATTC TATGGGCACG       1650

TCTTGCGAAA CCATCTTTTT AAACTCACCA GGCCCCTTCC CTTTCATCCA       1700

AGACAACATC TCCTTCTATG CGACCATTGG GCTCTGTCTC CCCTTCATTG       1750

TTGTTCTCAT TGTGTTGATC TGCCACAAAT ACAAAAAGCA ATTTAGGTAC       1800

GAGAGTCAGC TGCAGATGAT CCAGGTGACT GGCCCCCTGG ATAACGAGTA       1850

CTTCTACGTT GACTTCAGGG ACTATGAATA TGACCTTAAG TGGGAGTTCC       1900

CGAGAGAGAA CTTAGAGTTT GGGAAGGTCC TGGGGTCTGG CGCTTTCGGG       1950

AGGGTGATGA ACGCCACGGC CTATGGCATT AGTAAAACGG GAGTCTCAAT       2000

TCAGGTGGCG GTGAAGATGC TAAAAGAGAA AGCTGACAGC TGTGAAAAAG       2050

AAGCTCTCAT GTCGGAGCTC AAAATGATGA CCCACCTGGG ACACCATGAC       2100

AACATCGTGA ATCTGCTGGG GGCATGCACA CTGTCAGGGC CAGTGTACTT       2150

GATTTTTGAA TATTGTTGCT ATGGTGACCT CCTCAACTAC CTAAGAAGTA       2200

AAAGAGAGAA GTTTCACAGG ACATGGACAG AGATTTTTAA GGAACATAAT       2250

TTCAGTTTTT ACCCTACTTT CCAGGCACAT TCAAATTCCA GCATGCCTGG       2300

TTCACGAGAA GTTCAGTTAC ACCCGCCCTT GGATCAGCTC TCAGGGTTCA       2350

ATGGGAATTC AATTCATTCT GAAGATGAGA TTGAATATGA AAACCAGAAG       2400

AGGCTGGCAG AAGAAGAGGA GGAAGATTTG AACGTGCTGA CGTTTGAAGA       2450

CCTCCTTTGC TTTGCGTACC AAGTGGCCAA AGGCATGGAA TTCCTGGAGT       2500
```

| | |
|---|---|
| TCAAGTCGTG TGTCCACAGA GACCTGGCAG CCAGGAATGT GTTGGTCACC | 2550 |
| CACGGGAAGG TGGTGAAGAT CTGTGACTTT GGACTGGCCC GAGACATCCT | 2600 |
| GAGCGACTCC AGCTACGTCG TCAGGGGCAA CGCACGGCTG CCGGTGAAGT | 2650 |
| GGATGGCACC CGAGAGCTTA TTTGAAGGGA TCTACACAAT CAAGAGTGAC | 2700 |
| GTCTGGTCCT ACGGCATCCT TCTCTGGGAG ATATTTTCAC TGGGTGTGAA | 2750 |
| CCCTTACCCT GGCATTCCTG TCGACGCTAA CTTCTATAAA CTGATTCAGA | 2800 |
| GTGGATTTAA AATGGAGCAG CCATTCTATG CCACAGAAGG GATATACTTT | 2850 |
| GTAATGCAAT CCTGCTGGGC TTTTGACTCA AGGAAGCGGC CATCCTTCCC | 2900 |
| CAACCTGACT TCATTTTTAG GATGTCAGCT GGCAGAGGCA GAAGAAGCGA | 2950 |
| TGTATCAGAA CATGGGTGGC AACGTCCCAG AACATCCATC CATCTACCAA | 3000 |
| AACAGGCGGC CCCTCAGCAG AGAGGCGGGC TCAGAGCCGC CATCGCCACA | 3050 |
| GGCCCAGGTG AAGATTCACA GAGAAAGAAG TTAGCGAGGA GGCCTTGGAC | 3100 |
| CCCGCCACCC TAGCAGGCTG TAGACCGCAG AGCCAAGATT AGCCTCGCCT | 3150 |
| CTGAGGAAGC GCCCTACAGG CCGTTGCTTC GCTGGACTTT TCTCTAGATG | 3200 |
| CTGTCTGCCA TTACTCCAAA GTGACTTCTA TAAAATCAAA CCTCTCCTCG | 3250 |
| CACAGGCGGG AGAGCCAATA ATGAGACTTG TTGGTGAGCC CGCCTACCCT | 3300 |
| GGGGGGCCTT TCCAGGCCCC CCAGGCTTGA GGGGAAAGCC ATGTATCTGA | 3350 |
| AATATAGTAT ATTCTTGTAA ATACGTGAAA CAAACCAAAC CCGTTTTTTG | 3400 |
| CTAAGGGAAA GCTAAATATG ATTTTTAAAA ATCTATGTTT TAAAATACTA | 3450 |
| TGTAACTTTT TCATCTATTT AGTGATATAT TTTATGGATG GAAATAAACT | 3500 |
| TTCTACTGTA GAAAAAAAAA A | 3521 |

(2) INFORMATION FOR SEQ ID NO:2:

(i) SEQUENCE CHARACTERISTICS:
        (A) LENGTH: 1000 amino acids
        (B) TYPE: amino acid
        (D) TOPOLOGY: linear (xi) SEQUENCE DESCRIPTION: SEQ ID NO:2:

```
Met Arg Ala Leu Ala Gln Arg Ser Asp Arg Arg Leu Leu Leu Leu
 1               5                  10                  15

Val Val Leu Ser Val Met Ile Leu Glu Thr Val Thr Asn Gln Asp
                20                  25                  30

Leu Pro Val Ile Lys Cys Val Leu Ile Ser His Glu Asn Asn Gly
                35                  40                  45

Ser Ser Ala Gly Lys Pro Ser Ser Tyr Arg Met Val Arg Gly Ser
                50                  55                  60

Pro Glu Asp Leu Gln Cys Thr Pro Arg Arg Gln Ser Glu Gly Thr
                65                  70                  75

Val Tyr Glu Ala Ala Thr Val Glu Val Ala Glu Ser Gly Ser Ile
                80                  85                  90

Thr Leu Gln Val Gln Leu Ala Thr Pro Gly Asp Leu Ser Cys Leu
                95                 100                 105

Trp Val Phe Lys His Ser Ser Leu Gly Cys Gln Pro His Phe Asp
               110                 115                 120

Leu Gln Asn Arg Gly Ile Val Ser Met Ala Ile Leu Asn Val Thr
               125                 130                 135

Glu Thr Gln Ala Gly Glu Tyr Leu Leu His Ile Gln Ser Glu Ala
```

-continued

```
                140                 145                 150
Ala Asn Tyr Thr Val Leu Phe Thr Val Asn Val Arg Asp Thr Gln
                    155                 160                 165
Leu Tyr Val Leu Arg Arg Pro Tyr Phe Arg Lys Met Glu Asn Gln
                    170                 175                 180
Asp Ala Leu Leu Cys Ile Ser Glu Gly Val Pro Glu Pro Thr Val
                    185                 190                 195
Glu Trp Val Leu Cys Ser Ser His Arg Glu Ser Cys Lys Glu Glu
                    200                 205                 210
Gly Pro Ala Val Val Arg Lys Glu Glu Lys Val Leu His Glu Leu
                    215                 220                 225
Phe Gly Thr Asp Ile Arg Cys Cys Ala Arg Asn Ala Leu Gly Arg
                    230                 235                 240
Glu Ser Thr Lys Leu Phe Thr Ile Asp Leu Asn Gln Ala Pro Gln
                    245                 250                 255
Ser Thr Leu Pro Gln Leu Phe Leu Lys Val Gly Glu Pro Leu Trp
                    260                 265                 270
Ile Arg Cys Lys Ala Ile His Val Asn His Gly Phe Gly Leu Thr
                    275                 280                 285
Trp Glu Leu Glu Asp Lys Ala Leu Glu Glu Gly Ser Tyr Phe Glu
                    290                 295                 300
Met Ser Thr Tyr Ser Thr Asn Arg Thr Met Ile Arg Ile Leu Leu
                    305                 310                 315
Ala Phe Val Ser Ser Val Gly Arg Asn Asp Thr Gly Tyr Tyr Thr
                    320                 325                 330
Cys Ser Ser Ser Lys His Pro Ser Gln Ser Ala Leu Val Thr Ile
                    335                 340                 345
Leu Glu Lys Gly Phe Ile Asn Ala Thr Ser Ser Gln Glu Glu Tyr
                    350                 355                 360
Glu Ile Asp Pro Tyr Glu Lys Phe Cys Phe Ser Val Arg Phe Lys
                    365                 370                 375
Ala Tyr Pro Arg Ile Arg Cys Thr Trp Ile Phe Ser Gln Ala Ser
                    380                 385                 390
Phe Pro Cys Glu Gln Arg Gly Leu Glu Asp Gly Tyr Ser Ile Ser
                    395                 400                 405
Lys Phe Cys Asp His Lys Asn Lys Pro Gly Glu Tyr Ile Phe Tyr
                    410                 415                 420
Ala Glu Asn Asp Asp Ala Gln Phe Thr Lys Met Phe Thr Leu Asn
                    425                 430                 435
Ile Arg Lys Lys Pro Gln Val Leu Ala Asn Ala Ser Ala Ser Gln
                    440                 445                 450
Ala Ser Cys Ser Ser Asp Gly Tyr Pro Leu Pro Ser Trp Thr Trp
                    455                 460                 465
Lys Lys Cys Ser Asp Lys Ser Pro Asn Cys Thr Glu Glu Ile Pro
                    470                 475                 480
Glu Gly Val Trp Asn Lys Lys Ala Asn Arg Lys Val Phe Gly Gln
                    485                 490                 495
Trp Val Ser Ser Ser Thr Leu Asn Met Ser Glu Ala Gly Lys Gly
                    500                 505                 510
Leu Leu Val Lys Cys Cys Ala Tyr Asn Ser Met Gly Thr Ser Cys
                    515                 520                 525
Glu Thr Ile Phe Leu Asn Ser Pro Gly Pro Phe Pro Phe Ile Gln
                    530                 535                 540
```

-continued

```
Asp Asn Ile Ser Phe Tyr Ala Thr Ile Gly Leu Cys Leu Pro Phe
                545                 550                 555
Ile Val Val Leu Ile Val Leu Ile Cys His Lys Tyr Lys Lys Gln
            560                 565                 570
Phe Arg Tyr Glu Ser Gln Leu Gln Met Ile Gln Val Thr Gly Pro
            575                 580                 585
Leu Asp Asn Glu Tyr Phe Tyr Val Asp Phe Arg Asp Tyr Glu Tyr
            590                 595                 600
Asp Leu Lys Trp Glu Phe Pro Arg Glu Asn Leu Glu Phe Gly Lys
            605                 610                 615
Val Leu Gly Ser Gly Ala Phe Gly Arg Val Met Asn Ala Thr Ala
            620                 625                 630
Tyr Gly Ile Ser Lys Thr Gly Val Ser Ile Gln Val Ala Val Lys
            635                 640                 645
Met Leu Lys Glu Lys Ala Asp Ser Cys Glu Lys Glu Ala Leu Met
            650                 655                 660
Ser Glu Leu Lys Met Met Thr His Leu Gly His His Asp Asn Ile
            665                 670                 675
Val Asn Leu Leu Gly Ala Cys Thr Leu Ser Gly Pro Val Tyr Leu
            680                 685                 690
Ile Phe Glu Tyr Cys Cys Tyr Gly Asp Leu Leu Asn Tyr Leu Arg
            695                 700                 705
Ser Lys Arg Glu Lys Phe His Arg Thr Trp Thr Glu Ile Phe Lys
            710                 715                 720
Glu His Asn Phe Ser Phe Tyr Pro Thr Phe Gln Ala His Ser Asn
            725                 730                 735
Ser Ser Met Pro Gly Ser Arg Glu Val Gln Leu His Pro Pro Leu
            740                 745                 750
Asp Gln Leu Ser Gly Phe Asn Gly Asn Ser Ile His Ser Glu Asp
            755                 760                 765
Glu Ile Glu Tyr Glu Asn Gln Lys Arg Leu Ala Glu Glu Glu
            770                 775                 780
Glu Asp Leu Asn Val Leu Thr Phe Glu Asp Leu Leu Cys Phe Ala
            785                 790                 795
Tyr Gln Val Ala Lys Gly Met Glu Phe Leu Glu Phe Lys Ser Cys
            800                 805                 810
Val His Arg Asp Leu Ala Ala Arg Asn Val Leu Val Thr His Gly
            815                 820                 825
Lys Val Val Lys Ile Cys Asp Phe Gly Leu Ala Arg Asp Ile Leu
            830                 835                 840
Ser Asp Ser Ser Tyr Val Val Arg Gly Asn Ala Arg Leu Pro Val
            845                 850                 855
Lys Trp Met Ala Pro Glu Ser Leu Phe Glu Gly Ile Tyr Thr Ile
            860                 865                 870
Lys Ser Asp Val Trp Ser Tyr Gly Ile Leu Leu Trp Glu Ile Phe
            875                 880                 885
Ser Leu Gly Val Asn Pro Tyr Pro Gly Ile Pro Val Asp Ala Asn
            890                 895                 900
Phe Tyr Lys Leu Ile Gln Ser Gly Phe Lys Met Glu Gln Pro Phe
            905                 910                 915
Tyr Ala Thr Glu Gly Ile Tyr Phe Val Met Gln Ser Cys Trp Ala
            920                 925                 930
Phe Asp Ser Arg Lys Arg Pro Ser Phe Pro Asn Leu Thr Ser Phe
            935                 940                 945
```

```
Leu Gly Cys Gln Leu Ala Glu Ala Glu Ala Met Tyr Gln Asn
                950                 955                 960

Met Gly Gly Asn Val Pro Glu His Pro Ser Ile Tyr Gln Asn Arg
                965                 970                 975

Arg Pro Leu Ser Arg Glu Ala Gly Ser Glu Pro Pro Ser Pro Gln
                980                 985                 990

Ala Gln Val Lys Ile His Arg Glu Arg Ser
                995                 1000

(2) INFORMATION FOR SEQ ID NO:3:

(i) SEQUENCE CHARACTERISTICS:
         (A) LENGTH: 3475 bases
         (B) TYPE: nucleic acid
         (C) STRANDEDNESS: single
         (D) TOPOLOGY: linear (xi) SEQUENCE DESCRIPTION: SEQ ID NO:3:
```

| | |
|---|---|
| CGAGGCGGCA TCCGAGGGCT GGGCCGGCGC CCTGGGGGAC CCCGGGCTCC | 50 |
| GGAGGCCATG CCGGCGTTGG CGCGCGACGC GGGCACCGTG CCGCTGCTCG | 100 |
| TTGTTTTTTC TGCAATGATA TTTGGGACTA TTACAAATCA AGATCTGCCT | 150 |
| GTGATCAAGT GTGTTTTAAT CAATCATAAG AACAATGATT CATCAGTGGG | 200 |
| GAAGTCATCA TCATATCCCA TGGTATCAGA ATCCCCGGAA GACCTCGGGT | 250 |
| GTGCGTTGAG ACCCCAGAGC TCAGGACAG TGTACGAAGC TGCCGCTGTG | 300 |
| GAAGTGGATG TATCTGCTTC CATCACACTG CAAGTGCTGG TCGATGCCCC | 350 |
| AGGGAACATT TCCTGTCTCT GGGTCTTTAA GCACAGCTCC CTGAATTGCC | 400 |
| AGCCACATTT TGATTTACAA AACAGAGGAG TTGTTTCCAT GGTCATTTTG | 450 |
| AAAATGACAG AAACCCAAGC TGGAGAATAC CTACTTTTTA TTCAGAGTGA | 500 |
| AGCTACCAAT TACACAATAT TGTTTACAGT GAGTATAAGA AATACCCTGC | 550 |
| TTTACACATT AAGAAGACCT TACTTTAGAA AAATGGAAAA CCAGGACGCC | 600 |
| CTGGTCTGCA TATCTGAGAG CGTTCCAGAG CCGATCGTGG AATGGGTGCT | 650 |
| TTGCGATTCA CAGGGGGAAA GCTGTAAAGA AGAAAGTCCA GCTGTTGTTA | 700 |
| AAAAGGAGGA AAAAGTGCTT CATGAATTAT TTGGGACGGA CATAAGGTGC | 750 |
| TGTGCCAGAA ATGAACTGGG CAGGGAATGC ACCAGGCTGT TCACAATAGA | 800 |
| TCTAAATCAA ACTCCTCAGA CCACATTGCC ACAATTATTT CTTAAAGTAG | 850 |
| GGGAACCCTT ATGGATAAGG TGCAAAGCTG TTCATGTGAA CCATGGATTC | 900 |
| GGGCTCACCT GGGAATTAGA AAACAAAGCA CTCGAGGAGG GCAACTACTT | 950 |
| TGAGATGAGT ACCTATTCAA CAAACAGAAC TATGATACGG ATTCTGTTTG | 1000 |
| CTTTTGTATC ATCAGTGGCA AGAAACGACA CCGGATACTA CACTTGTTCC | 1050 |
| TCTTCAAAGC ATCCCAGTCA ATCAGCTTTG GTTACCATCG TAGGAAAGGG | 1100 |
| ATTTATAAAT GCTACCAATT CAAGTGAAGA TTATGAAATT GACCAATATG | 1150 |
| AAGAGTTTTG TTTTTCTGTC AGGTTTAAAG CCTACCCACA AATCAGATGT | 1200 |
| ACGTGGACCT TCTCTCGAAA ATCATTTCCT TGTGAGCAAA AGGGTCTTGA | 1250 |
| TAACGGATAC AGCATATCCA AGTTTTGCAA TCATAAGCAC CAGCCAGGAG | 1300 |
| AATATATATT CCATGCAGAA AATGATGATG CCCAATTTAC CAAAATGTTC | 1350 |
| ACGCTGAATA TAAGAAGGAA ACCTCAAGTG CTCGCAGAAG CATCGGCAAG | 1400 |

| | |
|---|---|
| TCAGGCGTCC TGTTTCTCGG ATGGATACCC ATTACCATCT TGGACCTGGA | 1450 |
| AGAAGTGTTC AGACAAGTCT CCCAACTGCA CAGAAGAGAT CACAGAAGGA | 1500 |
| GTCTGGAATA GAAAGGCTAA CAGAAAAGTG TTTGGACAGT GGGTGTCGAG | 1550 |
| CAGTACTCTA AACATGAGTG AAGCCATAAA AGGGTTCCTG GTCAAGTGCT | 1600 |
| GTGCATACAA TTCCCTTGGC ACATCTTGTG AGACGATCCT TTTAAACTCT | 1650 |
| CCAGGCCCCT TCCCTTTCAT CCAAGACAAC ATCTCATTCT ATGCAACAAT | 1700 |
| TGGTGTTTGT CTCCTCTTCA TTGTCGTTTT AACCCTGCTA ATTTGTCACA | 1750 |
| AGTACAAAAA GCAATTTAGG TATGAAAGCC AGCTACAGAT GGTACAGGTG | 1800 |
| ACCGGCTCCT CAGATAATGA GTACTTCTAC GTTGATTTCA GAGAATATGA | 1850 |
| ATATGATCTC AAATGGGAGT TTCCAAGAGA AAATTTAGAG TTTGGGAAGG | 1900 |
| TACTAGGATC AGGTGCTTTT GGAAAAGTGA TGAACGCAAC AGCTTATGGA | 1950 |
| ATTAGCAAAA CAGGAGTCTC AATCCAGGTT GCCGTCAAAA TGCTGAAAGA | 2000 |
| AAAAGCAGAC AGCTCTGAAA GAGAGGCACT CATGTCAGAA CTCAAGATGA | 2050 |
| TGACCCAGCT GGGAAGCCAC GAGAATATTG TGAACCTGCT GGGGGCGTGC | 2100 |
| ACACTGTCAG GACCAATTTA CTTGATTTTT GAATACTGTT GCTATGGTGA | 2150 |
| TCTTCTCAAC TATCTAAGAA GTAAAAGAGA AAAATTTCAC AGGACTTGGA | 2200 |
| CAGAGATTTT CAAGGAACAC AATTTCAGTT TTTACCCCAC TTTCCAATCA | 2250 |
| CATCCAAATT CCAGCATGCC TGGTTCAAGA GAAGTTCAGA TACACCCGGA | 2300 |
| CTCGGATCAA ATCTCAGGGC TTCATGGGAA TTCATTTCAC TCTGAAGATG | 2350 |
| AAATTGAATA TGAAAACCAA AAAAGGCTGG AAGAAGAGGA GGACTTGAAT | 2400 |
| GTGCTTACAT TTGAAGATCT TCTTTGCTTT GCATATCAAG TTGCCAAAGG | 2450 |
| AATGGAATTT CTGGAATTTA AGTCGTGTGT TCACAGAGAC CTGGCCGCCA | 2500 |
| GGAACGTGCT TGTCACCCAC GGGAAAGTGG TGAAGATATG TGACTTTGGA | 2550 |
| TTGGCTCGAG ATATCATGAG TGATTCCAAC TATGTTGTCA GGGGCAATGC | 2600 |
| CCGTCTGCCT GTAAAATGGA TGGCCCCCGA AAGCCTGTTT GAAGGCATCT | 2650 |
| ACACCATTAA GAGTGATGTC TGGTCATATG GAATATTACT GTGGGAAATC | 2700 |
| TTCTCACTTG GTGTGAATCC TTACCCTGGC ATTCCGGTTG ATGCTAACTT | 2750 |
| CTACAAACTG ATTCAAAATG GATTAAAAAT GGATCAGCCA TTTTATGCTA | 2800 |
| CAGAAGAAAT ATACATTATA ATGCAATCCT GCTGGGCTTT TGACTCAAGG | 2850 |
| AAACGGCCAT CCTTCCCTAA TTTGACTTCG TTTTTAGGAT GTCAGCTGGC | 2900 |
| AGATGCAGAA GAAGCGATGT ATCAGAATGT GGATGGCCGT GTTTCGGAAT | 2950 |
| GTCCTCACAC CTACCAAAAC AGGCGACCTT TCAGCAGAGA GATGGATTTG | 3000 |
| GGGCTACTCT CTCCGCAGGC TCAGGTCGAA GATTCGTAGA GGAACAATTT | 3050 |
| AGTTTTAAGG ACTTCATCCC TCCACCTATC CCTAACAGGC TGTAGATTAC | 3100 |
| CAAAACAAGA TTAATTTCAT CACTAAAAGA AAATCTATTA TCAACTGCTG | 3150 |
| CTTCACCAGA CTTTTCTCTA GAAGCCGTCT GCGTTTACTC TTGTTTTCAA | 3200 |
| AGGGACTTTT GTAAAATCAA ATCATCCTGT CACAAGGCAG GAGGAGCTGA | 3250 |
| TAATGAACTT TATTGGAGCA TTGATCTGCA TCCAAGGCCT TCTCAGGCCG | 3300 |
| GCTTGAGTGA ATTGTGTACC TGAAGTACAG TATATTCTTG TAAATACATA | 3350 |
| AAACAAAAGC ATTTTGCTAA GGAGAAGCTA ATATGATTTT TTAAGTCTAT | 3400 |

```
GTTTTAAAAT AATATGTAAA TTTTTCAGCT ATTTAGTGAT ATATTTTATG           3450

GGTGGGAATA AAATTTCTAC TACAG                                      3475
```

(2) INFORMATION FOR SEQ ID NO:4:

(i) SEQUENCE CHARACTERISTICS:
        (A) LENGTH: 993 amino acids
        (B) TYPE: amino acid
        (D) TOPOLOGY: linear (xi) SEQUENCE DESCRIPTION: SEQ ID NO:4:

```
Met Pro Ala Leu Ala Arg Asp Gly Gly Gln Leu Pro Leu Leu Val
 1               5                  10                  15

Val Phe Ser Ala Met Ile Phe Gly Thr Ile Thr Asn Gln Asp Leu
                20                  25                  30

Pro Val Ile Lys Cys Val Leu Ile Asn His Lys Asn Asn Asp Ser
                35                  40                  45

Ser Val Gly Lys Ser Ser Ser Tyr Pro Met Val Ser Glu Ser Pro
                50                  55                  60

Glu Asp Leu Gly Cys Ala Leu Arg Pro Gln Ser Ser Gly Thr Val
                65                  70                  75

Tyr Glu Ala Ala Ala Val Glu Val Asp Val Ser Ala Ser Ile Thr
                80                  85                  90

Leu Gln Val Leu Val Asp Ala Pro Gly Asn Ile Ser Cys Leu Trp
                95                 100                 105

Val Phe Lys His Ser Ser Leu Asn Cys Gln Pro His Phe Asp Leu
               110                 115                 120

Gln Asn Arg Gly Val Val Ser Met Val Ile Leu Lys Met Thr Glu
               125                 130                 135

Thr Gln Ala Gly Glu Tyr Leu Leu Phe Ile Gln Ser Glu Ala Thr
               140                 145                 150

Asn Tyr Thr Ile Leu Phe Thr Val Ser Ile Arg Asn Thr Leu Leu
               155                 160                 165

Tyr Thr Leu Arg Arg Pro Tyr Phe Arg Lys Met Glu Asn Gln Asp
               170                 175                 180

Ala Leu Val Cys Ile Ser Glu Ser Val Pro Glu Pro Ile Val Glu
               185                 190                 195

Trp Val Leu Cys Asp Ser Gln Gly Glu Ser Cys Lys Glu Glu Ser
               200                 205                 210

Pro Ala Val Val Lys Lys Glu Glu Lys Val Leu His Glu Leu Phe
               215                 220                 225

Gly Met Asp Ile Arg Cys Cys Ala Arg Asn Glu Leu Gly Arg Glu
               230                 235                 240

Cys Thr Arg Leu Phe Thr Ile Asp Leu Asn Gln Thr Pro Gln Thr
               245                 250                 255

Thr Leu Pro Gln Leu Phe Leu Lys Val Gly Glu Pro Leu Trp Ile
               260                 265                 270

Arg Cys Lys Ala Val His Val Asn His Gly Phe Gly Leu Thr Trp
               275                 280                 285

Glu Leu Glu Asn Lys Ala Leu Glu Glu Gly Asn Tyr Phe Glu Met
               290                 295                 300

Ser Thr Tyr Ser Thr Asn Arg Thr Met Ile Arg Ile Leu Phe Ala
               305                 310                 315

Phe Val Ser Ser Val Ala Arg Asn Asp Thr Gly Tyr Tyr Thr Cys
               320                 325                 330
```

-continued

```
Ser Ser Ser Lys His Pro Ser Gln Ser Ala Leu Val Thr Ile Val
            335                 340                 345

Glu Lys Gly Phe Ile Asn Ala Thr Asn Ser Ser Glu Asp Tyr Glu
            350                 355                 360

Ile Asp Gln Tyr Glu Glu Phe Cys Phe Ser Val Arg Phe Lys Ala
            365                 370                 375

Tyr Pro Gln Ile Arg Cys Thr Trp Thr Phe Ser Arg Lys Ser Phe
            380                 385                 390

Pro Cys Glu Gln Lys Gly Leu Asp Asn Gly Tyr Ser Ile Ser Lys
            395                 400                 405

Phe Cys Asn His Lys His Gln Pro Gly Glu Tyr Ile Phe His Ala
            410                 415                 420

Glu Asn Asp Asp Ala Gln Phe Thr Lys Met Phe Thr Leu Asn Ile
            425                 430                 435

Arg Arg Lys Pro Gln Val Leu Ala Glu Ala Ser Ala Ser Gln Ala
            440                 445                 450

Ser Cys Phe Ser Asp Gly Tyr Pro Leu Pro Ser Trp Thr Trp Lys
            455                 460                 465

Lys Cys Ser Asp Lys Ser Pro Asn Cys Thr Glu Glu Ile Thr Glu
            470                 475                 480

Gly Val Trp Asn Arg Lys Ala Asn Arg Lys Val Phe Gly Gln Trp
            485                 490                 495

Val Ser Ser Ser Thr Leu Asn Met Ser Glu Ala Ile Lys Gly Phe
            500                 505                 510

Leu Val Lys Cys Cys Ala Tyr Asn Ser Leu Gly Thr Ser Cys Glu
            515                 520                 525

Thr Ile Leu Leu Asn Ser Pro Gly Pro Phe Pro Phe Ile Gln Asp
            530                 535                 540

Asn Ile Ser Phe Tyr Ala Thr Ile Gly Val Cys Leu Leu Phe Ile
            545                 550                 555

Val Val Leu Thr Leu Leu Ile Cys His Lys Tyr Lys Lys Gln Phe
            560                 565                 570

Arg Tyr Glu Ser Gln Leu Gln Met Val Gln Val Thr Gly Ser Ser
            575                 580                 585

Asp Asn Glu Tyr Phe Tyr Val Asp Phe Arg Glu Tyr Glu Tyr Asp
            590                 595                 600

Leu Lys Trp Glu Phe Pro Arg Glu Asn Leu Glu Phe Gly Lys Val
            605                 610                 615

Leu Gly Ser Gly Ala Phe Gly Lys Val Met Asn Ala Thr Ala Tyr
            620                 625                 630

Gly Ile Ser Lys Thr Gly Val Ser Ile Gln Val Ala Val Lys Met
            635                 640                 645

Leu Lys Glu Lys Ala Asp Ser Ser Glu Arg Glu Ala Leu Met Ser
            650                 655                 660

Glu Leu Lys Met Met Thr Gln Leu Gly Ser His Glu Asn Ile Val
            665                 670                 675

Asn Leu Leu Gly Ala Cys Thr Leu Ser Gly Pro Ile Tyr Leu Ile
            680                 685                 690

Phe Glu Tyr Cys Cys Tyr Gly Asp Leu Leu Asn Tyr Leu Arg Ser
            695                 700                 705

Lys Arg Glu Lys Phe His Arg Thr Trp Thr Glu Ile Phe Lys Glu
            710                 715                 720

His Asn Phe Ser Phe Tyr Pro Thr Phe Gln Ser His Pro Asn Ser
            725                 730                 735
```

-continued

```
Ser Met Pro Gly Ser Arg Glu Val Gln Ile His Pro Asp Ser Asp
            740                 745                 750

Gln Ile Ser Gly Leu His Gly Asn Ser Phe His Ser Glu Asp Glu
            755                 760                 765

Ile Glu Tyr Glu Asn Gln Lys Arg Leu Glu Glu Glu Asp Leu
            770                 775                 780

Asn Val Leu Thr Phe Glu Asp Leu Leu Cys Phe Ala Tyr Gln Val
            785                 790                 795

Ala Lys Gly Met Glu Phe Leu Glu Phe Lys Ser Cys Val His Arg
            800                 805                 810

Asp Leu Ala Ala Arg Asn Val Leu Val Thr His Gly Lys Val Val
            815                 820                 825

Lys Ile Cys Asp Phe Gly Leu Ala Arg Asp Ile Met Ser Asp Ser
            830                 835                 840

Asn Tyr Val Val Arg Gly Asn Ala Arg Leu Pro Val Lys Trp Met
            845                 850                 855

Ala Pro Glu Ser Leu Phe Glu Gly Ile Tyr Thr Ile Lys Ser Asp
            860                 865                 870

Val Trp Ser Tyr Gly Ile Leu Leu Trp Glu Ile Phe Ser Leu Gly
            875                 880                 885

Val Asn Pro Tyr Pro Gly Ile Pro Val Asp Ala Asn Phe Tyr Lys
            890                 895                 900

Leu Ile Gln Asn Gly Phe Lys Met Asp Gln Pro Phe Tyr Ala Thr
            905                 910                 915

Glu Glu Ile Tyr Ile Ile Met Gln Ser Cys Trp Ala Phe Asp Ser
            920                 925                 930

Arg Lys Arg Pro Ser Phe Pro Asn Leu Thr Ser Phe Leu Gly Cys
            935                 940                 945

Gln Leu Ala Asp Ala Glu Glu Ala Met Tyr Gln Asn Val Asp Gly
            950                 955                 960

Pro Val Ser Glu Cys Pro His Thr Tyr Gln Asn Arg Arg Pro Phe
            965                 970                 975

Ser Arg Glu Met Asp Leu Gly Leu Leu Ser Pro Gln Ala Gln Val
            980                 985                 990

Glu Asp Ser
    993
```